(12) United States Patent
Hashash et al.

(10) Patent No.: US 8,455,662 B2
(45) Date of Patent: Jun. 4, 2013

(54) FORMULATIONS FOR BENZIMIDAZOLYL PYRIDYL ETHERS

(75) Inventors: Ahmad Hashash, Pleasant Hill, CA (US); Sean Ritchie, Berkeley, CA (US); Kangwen Lin, Fremont, CA (US); Peng Shen, Hayward, CA (US); Augustus Okhamafe, Concord, CA (US); Rampurna Gullapalli, San Bruno, CA (US)

(73) Assignee: Novartis AG, Basel (CH)

( * ) Notice: Subject to any disclaimer, the term of this patent is extended or adjusted under 35 U.S.C. 154(b) by 592 days.

(21) Appl. No.: 12/374,383

(22) PCT Filed: Jul. 20, 2007

(86) PCT No.: PCT/US2007/016469
§ 371 (c)(1),
(2), (4) Date: Sep. 25, 2009

(87) PCT Pub. No.: WO2008/011154
PCT Pub. Date: Jan. 24, 2008

(65) Prior Publication Data
US 2010/0040677 A1 Feb. 18, 2010

Related U.S. Application Data

(60) Provisional application No. 60/832,715, filed on Jul. 21, 2006.

(51) Int. Cl.
| C07D 235/00 | (2006.01) |
| C07D 403/02 | (2006.01) |
| C07D 401/00 | (2006.01) |
| A61K 9/64 | (2006.01) |
| A61K 9/48 | (2006.01) |
| A61K 31/44 | (2006.01) |
| A01N 43/40 | (2006.01) |

(52) U.S. Cl.
USPC .......... 548/306.1; 548/304.4; 546/273.4; 514/338; 424/456; 424/463

(58) Field of Classification Search
USPC ..... 548/306.1, 304.4; 424/456, 463; 514/338; 546/338
See application file for complete search history.

(56) References Cited

U.S. PATENT DOCUMENTS

| 5,717,100 | A | 2/1998 | Selnick et al. |
| 6,037,136 | A | 3/2000 | Beach et al. |
| 6,204,467 | B1 | 3/2001 | Greenholtz, Jr. et al. |
| 6,268,391 | B1 | 7/2001 | Dickerson et al. |
| 6,358,932 | B1 | 3/2002 | Monia |
| 6,391,636 | B1 | 5/2002 | Monia |
| 6,458,813 | B1 | 10/2002 | Mantlo et al. |
| 6,696,084 | B2 * | 2/2004 | Pace et al. ............ 424/451 |
| 7,482,367 | B2 * | 1/2009 | Aikawa et al. ......... 514/338 |
| 7,732,465 | B2 | 6/2010 | Aikawa et al. |
| 2001/0006975 | A1 | 7/2001 | Wood et al. |
| 2001/0014679 | A1 | 8/2001 | Tang et al. |
| 2001/0016194 | A1 | 8/2001 | Strom et al. |
| 2002/0082192 | A1 | 6/2002 | Mehta et al. |
| 2002/0137774 | A1 | 9/2002 | Riedl et al. |
| 2003/0198666 | A1 * | 10/2003 | Abbas et al. ............ 424/452 |
| 2004/0131670 | A1 * | 7/2004 | Gao ...................... 424/456 |
| 2007/0049622 | A1 | 3/2007 | Dimitroff et al. |
| 2010/0234394 | A1 | 9/2010 | Aikawa et al. |

FOREIGN PATENT DOCUMENTS

| WO | WO 95/19978 A1 | 7/1995 |
| WO | 03/082272 | 10/2003 |
| WO | WO 03/082272 | 10/2003 |
| WO | WO2005/112932 | * 1/2005 |
| WO | WO 2005/032548 | 4/2005 |

OTHER PUBLICATIONS

Payman Amiri, et al, CHIR-265 is a Potent Selective Inhibitor of c-Raf/B-Raf/mutB-Raf that Effectively Inhibits Proliferation and Survival of Cancer Cell Lines with Ras/Raf Pathway Mutations, 47 Proc. Am. Assoc. Cancer Res. 4855 (Apr. 4, 2006).*
Stephen Breyer, RAF Modulators and Methods of Use, 16 Expert Opin. Ther. Patents 1031 (2006).*
Eleni Venetsanakos, et al, CHIR-265, A Novel Inhibitor that Targets B-Raf and VEGFR, Shows Efficacy in a Broad Range of Preclinical Models, 47 Proc. Am. Assoc. Cancer Res. 4854 (Apr. 4, 2006).*
Darrin Stuart, et al, Characterization of a Novel Raf Kinase Inhibitor that Causes Target Dependent Tumor Regression in Human Melanoma Xenografts Expressing Mutant B-Raf, 47 Proc. Am. Assoc. Cancer Res. 4856 (Apr. 4, 2006).*
Maria Karasarides, et al, B-RAF is a Therapeutic Target in Melanoma, 23 Oncogene 6292 (2004).*

(Continued)

*Primary Examiner* — Sean Basquill
(74) *Attorney, Agent, or Firm* — Foley & Lardner LLP

(57) ABSTRACT

Formulations are provided, comprising: a compound of Formula I, a pharmaceutically acceptable salt thereof, or a mixture of any two or more thereof; and an ingredient selected from a hydrophilic solvent, a lipophilic solvent, an emulsifier, or a mixture of any two or more thereof; wherein the compound of Formula I is:

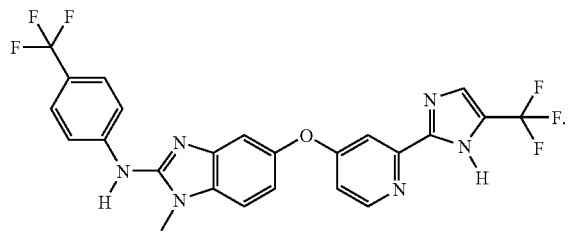

I

In some embodiments, the formulations are liquids. In other embodiments, the formulations are solids. Also provided are methods of preparing such formulations.

39 Claims, No Drawings

OTHER PUBLICATIONS

Srikala Sridhar, et al, Raf Kinase as a Target for Anticancer Therapeutics, 4 Mol. Cancer Ther. 677 (2005).*

Richard Bastin, et al, Salt Selection and Optimisation Procedures for Pharmaceutical New Chemical Entities, 4 Org. Proc. Res. Dev. 427 (2000).*

Colin Pouton, Formulation of Poorly Water-Soluble Drugs for Oral Administration: Physiochemical and Physiological Issues and the Lipid Formulation Classification System, 29 Eur. J Pharma. Sci. 278 (2006).*

Amidon, G.L., et al., "A theoretical basis for a biopharmaceutic drug classification: the correlation of in vitro drug product dissolution and in vivo bioavailability", *Pharm. Res.*, 12: 413-420 (1995).

Connolly, D., et al., "Human Vascular Permeability Factor", *J. Biol. Chem.* 264(33): 20017-20024 (1989).

Connolly, D., et al., "Tumor Vascular Permeability Factor Stimulates Endothelial Cell Growth and Angiogenesis", *J. Clin. Invest.* 84:1470-1478 (1989).

Crump, M. "Inhibition of raf kinase in the treatment of acute myeloid leukemia", *Curr. Pharm. Des.* 8: 2243-2248 (2002).

Ferrara, N., et al., "The Biology of Vascular Endothelial Growth Factor", *Endocrinol. Rev.* 18: 4-25 (1997).

*Guidance for Industry: Waiver of in Vivo Bioavailability and Bioequivalence Studies for Immediate-Release Solid Oral Dosage Forms Based on a Biopharmaceutics Classification System*, U.S. Department of Health and Human Services Food and Drug Administration Center for Drug Evaluation and Research (CDER), (Aug. 2000).

Hotte, S., et. al., "BAY 43/9006: Early clinical data in patients with advanced solid malignancies", *Current Pharmaceutical Design* 8: 2249-2253 (2002).

Leung, D., et al., "Vascular endothelial growth factor is a secreted angiogenic mitogen", *Science* 246: 1306-1309 (1989).

Mustonen, T., et al., "Endothelial receptor tyrosine kinases involved in angiogenesis", *J. Cell Biology*, 129(4): 895-898 (1995).

Plouet, J., et al., "Isolation and characterization of a newly identified endothelial cell mitogen produced by AtT-20 cells", *Embo. J.* 8:(12) 3801-3806 (1989).

Van Der Geer, P., et al. "Receptor Protein-Tyrosine Kinases and their Signal Transduction Pathways", *Annu. Rev. Cell Biol.*, 10: 251-337 (1994).

Bataille, V. A review of recent journal highlights. Clinical and Experimental Dermatology, 2006, vol. 31, No. 6, p. 617-619.

Burley S. Cancer and kinases: reports from the front line. Genome Biology, 2006, vol. 7, No. 4, Article 314.

* cited by examiner

FORMULATIONS FOR BENZIMIDAZOLYL PYRIDYL ETHERS

This application claims benefit of U.S. Provisional Application No. 60/832,715, filed Jul. 21, 2006, which in its entirety is herein incorporated by reference.

FIELD OF THE INVENTION

This invention pertains generally to formulations of benzimidazolyl pyridyl ether compounds. More specifically, the disclosure herein pertains to dosage formulations comprising, {1-methyl-5-[2-(5-trifluoromethyl-1H-imidazol-2-yl)-pyridin-4-yloxy]-1H-benzoimidazol-2-yl}-(4-trifluoromethyl-phenyl)amine, a tautomer thereof, a pharmaceutically acceptable salt thereof, a pharmaceutically acceptable salt of the tautomer thereof, or a mixture of any two or more thereof, and to methods for preparing and using such formulations.

BACKGROUND

The involvement of kinases in the development of cancer is well known. For example, kinases known to be associated with tumorigenesis include the Raf serine/threonine kinases and the receptor tyrosine kinases (RTKs). Both types of kinases are part of a signal transduction pathway which ultimately phosphorylate transcription factors. Within the pathway, Raf kinases are part of the Ras/Mitogen-Activated Protein Kinase (MAPK) signaling module that influence and regulate many cellular functions such as proliferation, differentiation, survival, oncogenic transformation and apoptosis.

Several Raf kinase inhibitors have been described as exhibiting efficacy in inhibiting tumor cell proliferation in vitro and/or in vivo assays (see, e.g., U.S. Pat. Nos. 6,391,636, 6,358,932, 6,037,136, 5,717,100, 6,458,813, 6,204,467, and 6,268,391). Other patents and patent applications suggest the use of Raf kinase inhibitors for treating leukemia (see, e.g., U.S. Pat. Nos. 6,268,391, and 6,204,467, and published U.S. Patent Application Nos. 20020137774; 20020082192; 20010016194; and 20010006975), or for treating breast cancer (see, e.g., U.S. Pat. Nos. 6,358,932; 5,717,100; 6,458,813; 6,268,391; and 6,204,467, and published U.S. Patent Application No. 20010014679). In early clinical trials, inhibitors of Raf-1 kinase that also inhibit B-Raf have shown promise as therapeutic agents in cancer therapy (Crump, *Current Pharmaceutical Design* 8:2243-2248 (2002); Sebastien et al., *Current Pharmaceutical Design* 8: 2249-2253 (2002)).

Receptor tyrosine kinases (RTKs), such as vascular endothelial growth factor receptors (VEGFR), are transmembrane polypeptides that regulate developmental cell growth and differentiation, remodeling, and regeneration of adult tissues. Mustonen, T. et al., *J. Cell Biology* 129:895-898 (1995); van der Geer, P. et al., *Ann Rev. Cell Biol.* 10:251-337 (1994). VEGF and members of the VEGF subfamily are able to induce vascular permeability and endothelial cell migration and proliferation, as well as induce angiogenesis and vasculogenesis. Ferrara, N. et al., *Endocrinol. Rev.* 18:4-25 (1997); Connolly, D. et al., *J. Biol. Chem.* 264:20017-20024 (1989); Connolly, D. et al., *J. Clin. Invest.* 84:1470-1478 (1989); Leung, D. et al., *Science* 246:1306-1309 (1989); Plouet, J. et al., *EMBO J* 8:3801-3806 (1989).

Angiogenesis is the process whereby new blood vessels are formed in a tissue, and is critical to the growth of cancer cells. In cancer, once a nest of cancer cells reaches a certain size, roughly 1 to 2 mm in diameter, the cancer cells must develop a blood supply in order for the tumor to grow larger as diffusion is not sufficient to supply the cancer cells with enough oxygen and nutrients. Thus, inhibition of angiogenesis by the inhibition of kinases involved in angiogenesis is expected to halt the growth of cancer cells.

One class of compounds that inhibit angiogenesis, inhibit the growth of tumors, treat cancer, modulate cell cycle arrest, and/or inhibit kinases such as Ras, Raf, mutant B-Raf, VEGFR2 (KDR, Flk-1), FGFR2/3, c-Kit, PDGFRβ, CSF-1R is the class of compounds known as benzimidazolyl pyridyl ethers. Methods for the synthesis and use of various benzimidazolyl pyridyl ether compounds have been disclosed in WO 2003/082272 and WO 2005/032458 and in U.S. Provisional Application Nos. 60/712,539 filed on Aug. 30, 2005; 60/731,591 filed on Oct. 27, 2005; 60/774,684 filed on Feb. 17, 2006; and 60/713,108 filed on Aug. 30, 2005, the entire disclosures of which are herein incorporated by reference for all purposes. Despite the excellent biological activity shown by benzimidazolyl pyridyl ethers, challenges in formulating this class of compounds exist due to the low water solubility of the compounds at physiological pH.

SUMMARY

In one aspect, formulations and medicaments of benzimidazolyl pyridyl ethers and methods of making and using such formulations and medicaments are provided. The formulations include solid and liquid formulations of {1-methyl-5-[2-(5-trifluoromethyl-1H-imidazol-2-yl)-pyridin-4-yloxy]-1H-benzoimidazol-2-yl}-(4-trifluoromethyl-phenyl)amine in capsule and tablet form, among others. The formulations may be administered orally or by other methods known in the art. Embodied formulations provide improved aqueous solubility and improved in-vivo exposure/pharmacokinetics of the benzimidazolyl pyridyl ether compounds compared to the unformulated compounds.

In one aspect, the present invention provides a formulation comprising a compound of Formula I, a pharmaceutically acceptable salt thereof, or a mixture of any two or more thereof, and an ingredient selected from a hydrophilic solvent, a lipophilic solvent, an emulsifier, or a mixture of any two or more thereof:

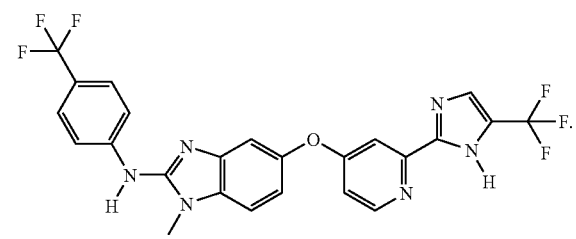

I

For example, the ingredient can be a mixture of hydrophilic solvent and lipophilic solvent, or a mixture of hydrophilic solvent, lipophilic solvent, and emulsifier.

In some embodiments, the formulation, comprises a compound of Formula I, a pharmaceutically acceptable salt thereof, or a mixture of any two or more thereof, a hydrophilic solvent, a lipophilic solvent, and an emulsifier.

In some embodiments, the formulation is a liquid formulation. In other embodiments, the formulation is a solid formulation.

In another aspect, formulations described herein may be contained within a capsule or tablet. In other embodiments, the total mass of the compound of Formula I, a pharmaceutically acceptable salt thereof, or a mixture of any two or more thereof, contained within the capsule or tablet, ranges from about 1 mg to about 400 mg, inclusive. In some embodiments, the capsule or tablet is coated with polymer or gelatin, or is encapsulated within a gelatin sheath. The capsule may be a hard shell capsule and may further have a band-sealed head section and a body section.

In another aspect, methods are provided for producing a formulation, comprising combining and/or mixing a compound of Formula I, a pharmaceutically acceptable salt thereof, or a mixture of any two or more thereof, with an ingredient selected from a hydrophilic solvent, a lipophilic solvent, an emulsifier, or a mixture of any two or more thereof, to form a formulation. The methods may further include combining the compound, salt or mixture and the ingredient with an antioxidant, a preservative, a sweetener, a flavoring agent, a coloring agent, or a mixture of any two or more thereof, to form a formulation. In some embodiments, the compound, salt, or mixture and the ingredient are combined using a formulation aid selected from, e.g., methanol, ethanol, or a mixture thereof.

There are also provided in some embodiments, a pharmaceutical packaging container, comprising: a storage vessel comprising one or more capsules or tablets, the one or more capsules or tablets comprising a formulation as embodied herein.

Inventive formulations are useful as pharmaceutical formulations or medicaments in the treatment of cancer and/or inhibition of angiogenesis in a subject in need thereof. Thus, in another aspect, there are provided methods for treating cancer and/or inhibiting angiogenesis in a subject, comprising administering the formulations to the subject. In some embodiments related to methods of treating cancer, the formulation is administered in an amount sufficient to provide a $C_{max}$ of from about 0.1 to about 10 μg/mL of the compound of Formula I, a pharmaceutically acceptable salt thereof, or a mixture of any two or more thereof, in the subject's plasma. In other embodiments of the method for treating cancer, the formulation is administered in an amount sufficient to provide to provide an AUC of about 0.01 to about 10 mg*min/mL of the compound of Formula I, a pharmaceutically acceptable salt thereof, or a mixture of any two or more thereof, in the subject's plasma. In such treatment methods, the formulation is administered once, twice, three, four times, or more daily or weekly. In other embodiments of the method for treating cancer, the cancer to be treated is bladder, breast, brain, carcinoma, chronic lymphoid leukemia, chronic myelogenous leukemia, colorectal, gastric, gastrointestinal stromal, glioma, lymphoma, melanoma, multiple myeloma, myeloproliferative disease, neuroendocrine, non-small cell lung, small cell lung, pancreatic, prostate, renal cell, small cell acute myelogenous leukemia, sarcoma, and/or thyroid cancers.

DETAILED DESCRIPTION

Formulations of benzimidazolyl pyridyl ether compounds are provided. Such formulations may be used to inhibit RAF kinase, an important kinase enzyme in the MAPK pathway. The formulations are useful, for example, in treating patients with cancer and/or a need for an inhibitor of RAF kinase.

The following abbreviations and definitions are used throughout this application:

"Adsorbent carrier" refers to materials, usually solid, employed to adsorb and/or absorb a liquid formulation.

"API" is an abbreviation for active pharmaceutical ingredient. As used herein, unless otherwise noted, API refers to the compound: {1-methyl-5-[2-(5-trifluoromethyl-1H-imidazol-2-yl)-pyridin-4-yloxy]-1H-benzoimidazol-2-yl}-(4-trifluoromethyl-phenyl)amine.

"AUC" is an abbreviation for area under the curve in a graph of the concentration of a compound in blood plasma over time.

"BCS" is an abbreviation for the Biopharmaceutics Classification System which is a scientific framework for classifying drug substances based on their aqueous solubility and intestinal permeability. See, for example, *Guidance for Industry: Waiver of In Vivo Bioavailability and Bioequivalence Studies for Immediate-Release Solid Oral Dosage Forms Based on a Biopharmaceutics Classification System*, U.S. Department of Health and Human Services Food and Drug Administration Center for Drug Evaluation and Research (CDER), August 2000; and Amidon, G. L., H. Lennernäs, V. P. Shah, and J. R. Crison, *Pharmaceutical Research*, 12:413-420 (1995).

"Cellulose" includes the various forms of cellulose known for use in pharmaceutical formulations, including but not limited to, ethyl cellulose, cellulose acetate, carboxymethyl cellulose calcium, sodium carboxymethyl cellulose, methyl cellulose, hydroxyethyl cellulose, hydroxypropyl cellulose, hydroxypropyl methyl cellulose, (e.g., Nos. 2208, 2906, 2910), hydroxypropylmethyl cellulose phthalate, microcrystalline cellulose, and mixtures thereof. Suitable forms of microcrystalline cellulose for use in formulations of the invention include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof.

"$C_{max}$" is an abbreviation that refers to the maximum observed concentration of a compound in the plasma, tissue, or blood of a subject to which the compound has been administered. $C_{max}$ typically occurs within several minutes to several hours following administration of a compound to a subject, and is dependent upon the intrinsic physicochemical and biological properties of the compound.

Croscarmellose sodium is cross-linked sodium carboxymethyl cellulose.

"Crospovidone" is a water-insoluble cross-linked homopolymer of 1-vinyl-2-pyrrolidinone typically having an empirically determined average molecular weight of greater than 1,000,000.

"Cyclodextrin" refers to a family of cyclic oligosaccharides containing at least six D-(+)-glucopyranose units.

"Emulsifier," as used herein, refers to a material that promotes the formation of an emulsion.

"Emulsion," as used herein, refers to a dispersion of one immiscible liquid in another liquid. "Microemulsion" refers to a clear isotropic liquid mixture of a lipophilic liquid, a hydrophilic liquid, and one or more surfactants.

"EtOAc" is an abbreviation for ethyl acetate.

"EtOH" is an abbreviation for ethanol.

"Fatty acid," as used herein, refers to any of the members of a large group of monobasic acids, especially those found in animal and vegetable fats and oils. In some embodiments the fatty acid is straight or branched chain alkyl or alkenyl group having 6 to 22 carbons, wherein the carboxylic acid is at one terminus of the carbon chain.

"Glycerides," as used herein, refers to esters formed between one or more acids and glycerol. In some embodiments, the acids are fatty acids. Medium-chain glycerides are glycerol esters of medium-chain fatty acids containing from 6 to 12 carbon atoms, or, in some embodiments, 6 to 10 carbon atoms. Medium chain fatty acids include: caproic acid (C6);

caprylic acid (C8), capric acid (C10), and lauric acid (C12) Long chain glycerides are glycerol esters of long chain fatty acids containing from 12 to 22 carbon atoms, or in some embodiments, 12 to 18 carbon atoms.

"HDPE" is an abbreviation for high density polyethylene.

"HGC" is an abbreviation for hard gelatin capsule.

"HPLC" is an abbreviation for high performance liquid chromatography.

"HPMC" is an abbreviation for hydroxypropyl methylcellulose.

"Hydrophilic," as used herein, refers to a material that readily dissolves in water or dissolves water. "Hydrophilic solvents" are solvents which dissolve or disperse a solute and which itself also dissolve in water or dissolve water.

"LAH" is an abbreviation for lithium aluminum hydride.

"Lipid," as used herein, refers to any of a group of organic compounds, including, but not limited to the fats, oils, waxes, sterols, and triglycerides, that are insoluble in water but soluble in nonpolar organic solvents, and are oily to the touch.

"Lipophilic," as used herein, refers to a material that readily dissolves in lipids or dissolves lipids. "Lipophilic solvents" are solvents which dissolve or disperse a solute and which itself dissolves in lipids or dissolves lipids.

"LCMS" is an abbreviation for liquid chromatography mass spectroscopy.

"MeOH" is an abbreviation for methanol.

"MPEG" is an abbreviation for methoxypolyethylene glycol, a polyether having the general formula $CH_3O[CH_2CH_2O]_nH$, and having a wide range of average molecular weight. As used herein and except as otherwise indicated, MPEG may have an average molecular weight of from about 100 to about 20,000 g/mol, or higher.

"MTBE" is an abbreviation for methyl-tert-butyl ether.

"NMR" is an abbreviation for nuclear magnetic resonance.

"PEG" is an abbreviation for polyethyleneglycol, a polyether polymer of polyethyleneoxide and having the general formula $HO[CH_2CH_2O]_nH$, and having a wide range of average molecular weight. In some embodiments, the PEG has an average molecular weight of from about 100 g/mol to about 1,000 g/mol. In some embodiments, the PEG has an average molecular weight of greater than about 1,000 g/mol. In other embodiments, the PEG has an average molecular weight of from about 1,000 g/mol to about 20,000 g$\mu$mol.

"Phospholipid," as used herein, refers to phosphorous-containing lipids that are composed mainly of fatty acids, a phosphate group, and a simple organic molecule, e.g. glycerol. Phospholipids may also be referred to as phosphatides.

"PEO" is an abbreviation for polyoxyethylene. As used herein, and except as otherwise indicated, polyoxyethylene is a polyether polymer of ethylene glycol having an average molecular weight of greater than 20,000 g/mol. In some embodiments, the average molecular weight of PEO is from greater than 20,000 up to 300,000 g/mol. PEO may be used in the form of copolymers with other polymers.

Povidone, as used herein, is a polymer of 1-vinyl-2-pyrrolidinone, and having a wide range of average molecular weight. In some embodiments, the povidone has an average molecular weight of from about 2,500 g/mol to about 300,000 g/mol, or greater.

"RH" is an abbreviation for relative humidity.

"rt" is an abbreviation for room temperature.

"SEDDS" is an abbreviation for self-emulsifying drug delivery systems.

"SMEDDS" is an abbreviation for self-microemulsifying drug delivery systems.

"Sorbitan," as used herein, refers to dehydrated Sorbitol.

"Starch" refers to a complex carbohydrate consisting of amylase and amylopectin. "Pregelatinized starch" is starch that has been chemically and/or mechanically processed to rupture all or part of the granules in the presence of water and subsequently dried. Some types of pregelatinized starch may be modified to render them compressible and flowable in character.

"Sugar fatty acid," as used herein, refers to a fatty acid with a sugar moiety attached.

"TBACl" is an abbreviation for tert-butylammonium chloride.

"TFAA" is an abbreviation for trifluoroacetic acid.

"THF" is an abbreviation for tetrahydrofuran.

"TLC" is an abbreviation for thin layer chromatograph.

A "pharmaceutically acceptable salt" includes a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanol amine, and triethanolamine. Salts of inorganic acids include, for example, hydrochloric acid, hydroboric acid, nitric acid, sulfuric acid, and phosphoric acid. Salts of organic acids include, for example, formic acid, acetic acid, fumaric acid, oxalic acid, tartaric acid, maleic acid, lactic acid, citric acid, succinic acid, malic acid, methanesulfonic acid, benzenesulfonic acid, and p-toluenesulfonic acid. Salts of basic amino acids include, for example, arginine, lysine and ornithine. Acidic amino acids include, for example, aspartic acid and glutamic acid.

The term "subject," as used herein, refers to any animal that can experience the beneficial effects of the formulations and methods embodied herein. Thus, a compound of Formula I, a pharmaceutically acceptable salt thereof, or mixtures of any two or more thereof may be administered to any animal that can experience the beneficial effects of the compound in accordance with the methods of treating cancer provided herein. Preferably, the animal is a mammal, and in particular a human, although it is not intended to be so limited. Examples of other suitable animals include, but are not limited to, rats, mice, monkeys, dogs, cats, cattle, horses, pigs, sheep, and the like.

"Treating," as used herein, refers to an alleviation of symptoms associated with a disorder or disease, or halt or slowing of further progression or worsening of those symptoms, or prevention or prophylaxis of the disease or disorder. For example, within the context of cancer, successful treatment may include an alleviation of symptoms, or halting or slowing the progression of the disease, as measured by a reduction in the growth rate of a tumor, a halt in the growth of the tumor, a reduction in the size of a tumor, partial or complete remission of the cancer, or increased survival rate or clinical benefit.

"Solvate," as used herein, refers to an association of a solvent with a compound, in the crystalline form. The solvent association is typically due to the use of the solvent in the synthesis, crystallization, and/or recrystallization of the compound.

"Hydrate," as used herein, refers to an association of water with a compound, in the crystalline form. The water association is typically due to the use of the water in the synthesis, crystallization, and/or recrystallization of the compound, and may also be a result of the hygroscopic nature of the compound.

"About," as used herein in conjunction with a stated numerical value, refers to a value within ±10% of the stated numerical value.

As used herein, and unless otherwise specified, "a" or "an" refers to "one or more."

It will be readily understood by those of skill in the art, that some materials identified below as belonging to a category such as a hydrophilic solvent, a lipophilic solvent, an emulsifier, an adsorbent carrier, a polymeric carrier, an additional ingredient, or as a coating material may fall into one or more of those categories, although not listed as part of the other categories. For example, hydroxypropyl cellulose is a polymer carrier in some embodiments, and/or may used as a coating for a capsule or tablet in other embodiments. As another example, the compound sold under the tradename GELUCIRE 44/14 may be both an emulsifier and a lipophilic solvent. Other such materials belonging in more than one category, but listed in only one category, will be readily identified by one of skill in the art.

Formulations of benzimidazolyl pyridyl ether compounds, in general, are provided. More specifically, the invention herein pertains to formulations comprising a compound of Formula I, a pharmaceutically acceptable salt thereof, or a mixture of any two or more thereof, and to methods for preparing and using such formulations. As used throughout this disclosure, Formula I refers to {1-methyl-5-[2-(5-trifluoromethyl-1H-imidazol-2-yl)-pyridin-4-yloxy]-1H-benzoimidazol-2-yl}-(4-trifluoromethyl-phenyl)amine, a compound having the structure:

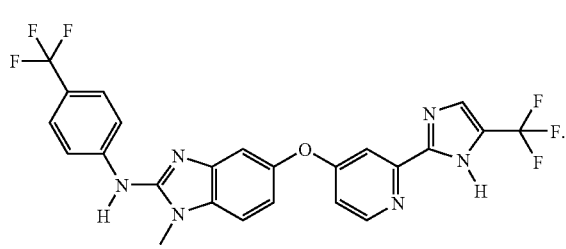

I

It will be understood by those of skill in the art, that a compound of Formula I, can also exist in the form of solvates and/or hydrates and that all such solvates and hydrates are encompassed by the compound and structure of Formula I.

It should also be understood that organic compounds according to the invention may exhibit the phenomenon of tautomerism. As a drawn chemical structure within the disclosure can only represent one possible tautomeric form at a time, it should be understood that the compound of Formula I encompasses any tautomeric form of the drawn structure. For example, one possible tautomer of the compound of Formula I is shown below as Tautomer Ia:

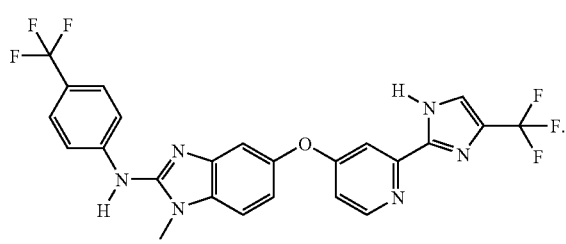

Ia

Those of skill in the art, will recognize and understand that the compound of Formula I, and tautomers thereof, may also exist in solvate and/or hydrate forms and are also encompassed by the compound and/or structure of Formula I. Likewise, pharmaceutically acceptable salts of the compound of Formula I also encompass the corresponding solvates and/or hydrates of the pharmaceutically acceptable salts of the compound of Formula I.

In some embodiments, formulations are disclosed comprising a compound of Formula I, a pharmaceutically acceptable salt thereof, or a mixture of any two or more thereof, and an ingredient selected from a hydrophilic solvent, a lipophilic solvent, an emulsifier, or a mixture of any two or more thereof. In some embodiments, the ingredient comprises a mixture of a hydrophilic solvent and a lipophilic solvent. In other embodiments, the ingredient comprises a mixture of a hydrophilic solvent, a lipophilic solvent, and an emulsifier.

Liquid Formulations

In one aspect, the formulations embodied herein are liquid formulations. In some such embodiments, hydrophilic solvents of the present disclosure are selected from, but are not limited to diethylene glycol monoethyl ether, ethanol, glycerin, glycofurol, a MPEG, N-methyl-2-pyrrolidone, a PEG, propylene carbonate, propylene glycol, or a mixture of any two or more thereof. In some embodiments, the PEG has an average molecular weight of from about 100 g/mol to about 1,000 g/mol. In some embodiments, the MPEG has an average molecular weight of from about 100 g/mol to about 1,000 gμmol.

In some embodiments, the hydrophilic solvent is ethanol, a PEG, or a mixture of any two or more thereof. In some such embodiments, the ethanol is present at a concentration of up to about 15% based upon the total weight of the formulation. In other such embodiments, the PEG is present at a concentration of up to about 90% based upon the total weight of the formulation.

Lipophilic solvents suitable for use in the embodied formulations may include, but are not limited to a fatty acid such as, but no limited to, linoleic, linolenic, oleic, palmitostearic acid, and stearic acid; a medium chain glyceride such as, but not limited to, glyceryl mono-, di-, or tri-caprylic and capric acid esters, also known as medium chain mono-, di-, and triglycerides and sold under tradenames such as MIGLYOL® 812, LABRAFAC CC®, and CAPMUL® MCM; a long chain glyceride (of $C_{12}$-$C_{18}$ fatty acids) such as, but not limited to, corn oil; cottonseed oil, glyceryl behenate, glyceryl monooleate, glyceryl monostearate, glyceryl palmitostearate, olive oil, peanut oil, peppermint oil, safflower oil, sesame oil, and soybean oil; a ethyl ester of a fatty acid such as ethyl linoleate and ethyl oleate; DL-α-tocopherol; a propylene glycol fatty acid ester such as, but not limited to, propylene glycol mono- or di-laureate; a sorbitan fatty acid ester such as, but not limited to, sorbitan monolaurate, sorbitan monooleate, sorbitan monopalmitate, sorbitan monostearate, and sorbitan trioleate; a polyglyceryl fatty acid ester formed from various glyceryl ethers and fatty acids. In some embodiments, the lipophilic solvent is oleic acid. In some embodiments, the lipophilic solvents are solids or semisolids at room temperature, even though the formulation prepared with the lipophilic solvent is a liquid formulation. Examples of polyglycerols used in esterification include diglycerol, tetraglycerol, hexaglycerol, decaglycerol, decaglycerol, and the like. Examples of fatty acids reacted with polyglycerols include oleic acid, linoleic acid, stearic acid, and the like. Examples of polyglyceryl fatty acid ester include PLUROL OLEIQUE CC 497 (polyglyceryl oleate; Gattefosse Co.), PLUROL STEARIQUE (polyglyceryl palmitostearate; Gattefosse Co.), DGMO-C (diglyceryl monooleate; Nikkol Co.), TETRAGLYN 1-O (tetraglyceryl monooleate; Nikkol Co.), HEXAGLYN 1-O (hexaglyceryl monooleate; Nikkol Co.), HEXAGLYN 5-O (hexaglyceryl pentaoleate; Nikkol Co.), DECAGLYN 5-O (Decaglyceryl pentaoleate; Nikkol Co.), DECAGLYN 10-O (Decaglyceryl decaoleate; Nikkol Co.), and the like.

Emulsifiers suitable for use in the embodied formulations may include, but are not limited to a sugar fatty acid ester; a polyoxyethylene sorbitan fatty acid ester such as, but not limited to, polysorbate 20, polysorbate 40, polysorbate 60, and polysorbate 80; a polyoxyethylene mono- and di-fatty acid ester including, but not limited to polyoxyl 40 stearate and polyoxyl 40 oleate; a mixture of polyoxyethylene mono- and di-esters of $C_8$-$C_{22}$ fatty acids and glyceryl mono-, di-, and tri-esters of $C_8$-$C_{22}$ fatty acids as sold under tradenames such as LABRASOL®, GELUCIRE® 44/14, GELUCIRE® 50/13, LABRAFIL® M 1944 CS, and LABRAFIL® M2125 CS; a polyoxyethylene castor oil compound such as, but not limited to, polyoxyl 35 castor oil, polyoxyl 40 hydrogenated castor oil, and polyoxyl 60 hydrogenated castor oil, as are sold under tradenames such as CREMOPHOR® ELP, CREMOPHOR® RH 40, and CREMOPHOR® RH 60, respectively; a polyoxyethylene alkyl ether including but not limited to polyoxyl 20 cetostearyl ether, and polyoxyl 10 oleyl ether; DL-α-tocopheryl polyethylene glycol succinate as may be sold under the tradename VITAMIN E TPGS®; a glyceryl mono-, di-, and tri-ester; a glyceryl mono-, di-, and tri-esters of $C_8$-$C_{22}$ fatty acid; a sucrose mono-, di-, and tri-ester; sodium dioctyl sulfosuccinate; sodium lauryl sulfate; or a mixture of any two or more thereof.

Liquid formulations embodied herein may also include pharmaceutically acceptable additives such as an antioxidant, a coloring agent, a flavoring agent, a preservative, a sweetener, or a mixture of any two or more thereof. Antioxidants suitable for use in the embodied formulations include, but are not limited to, ascorbic acid, ascorbyl palmitate, butylated hydroxyanisole, butylated hydroxytoluene, ethylenediaminetetraacetic acid, salts of ethylenediaminetetraacetic acid, propyl gallate, sodium metabisulfite, vitamin E, esters of Vitamin E, or a mixture of any two or more thereof. Preservatives suitable for use in the embodied formulations include, but are not limited to, butylparaben, calcium sorbate, ethylparaben, methylparaben, monothioglycerol, potassium sorbate, propylparaben, sodium benzoate, sodium sorbate, sorbic acid, or a mixture of any two or more thereof. Sweeteners suitable for use in the embodied formulations include, but are not limited to, aspartame, glycyrrhizin salts, monoammonium glycyrrhizinate, saccharin, saccharin calcium, saccharin sodium, sugar, sucralose, or a mixture of any two or more thereof. Flavoring agents suitable for use in the embodied formulations include, but are not limited to, citric acid, menthol, peppermint oil, sodium citrate, vanillin, ethyl vanillin, or a mixture of any two or more thereof. Coloring agents suitable for use in the embodied formulations include, but are not limited to, FD&C blue #1, FD&C blue #2, FD&C green #3, FD&C red #3, FD&C red #4, FD&C yellow #5, FD&C yellow #6, D&C blue #4, D&C green #5, D&C green #6, D&C orange #4, D&C orange #5, iron oxides, or a mixture of any two or more thereof.

The amount of active pharmaceutical ingredient in liquid formulations of the invention varies with the intended application, and it is well within the skill of those in the art to determine the appropriate amount for any particular application based on the disclosure herein. In some embodiments of the liquid formulations disclosed herein, the compound of Formula I, a pharmaceutically acceptable salt thereof, or a mixture of any two or more thereof, is present in an amount from about 0.1 wt % to about 40 wt % based upon the total weight of the formulation. In other such embodiments, the compound of Formula I, a pharmaceutically acceptable salt thereof, or a mixture of any two or more thereof, is present in an amount from about 0.2 wt % to about 20 wt % based upon the total weight of the formulation. In yet other embodiments, the compound of Formula I, a pharmaceutically acceptable salt thereof, or a mixture of any two or more thereof, is present in an amount from about 0.5 wt % to about 10 wt % based upon the total weight of the formulation.

In some embodiments, the hydrophilic solvent is present at up to about 90 wt % based upon the total weight of the formulation. In other embodiments, the emulsifier is present at from about 5 wt % to about 50 wt % based upon the total weight of the formulation. In yet other embodiments, the lipophilic solvent is present at up to about 50 wt % based upon the total weight of the formulation.

Liquid formulations may be contained within a capsule. In some embodiments, the capsule is a hard shell capsule, a hard gelatin capsule, a soft gelatin capsule, natural pullulan capsule, or a hydroxypropyl methylcellulose shell capsule. In some embodiments, the total mass of the compound of Formula I, a pharmaceutically acceptable salt thereof, or a mixture of any two or more thereof, in the capsule ranges from about 1 mg to about 400 mg. In some embodiments, the capsule is coated with polymer or gelatin, or is encapsulated within a gelatin sheath. The capsule may be hard shell capsule and may further have a band-sealed head section and a body section.

Formulations disclosed herein are stable. Table 5 in the Examples section details exemplary stability data for liquid formulations. Thus in some embodiments, the amount of degradants of the API in the embodied formulations, is typically less than 10% by weight based on the total weight of the formulation after storage of the formulation for three months at 50° C. and 75% relative humidity. In other embodiments, the amount of degradants is less than 8%, less than 5%, less than 4%, less than 3%, less than 2% or even less than 1% by weight based on the total weight of the formulation after storage of the formulation for three months at 50° C. and 75% relative humidity conditions.

Solid Formulations

In another aspect, the formulations embodied herein are solid formulations. In some such embodiments, the hydrophilic solvent includes, but is not limited to, a PEG, a MPEG, a PEO, or a mixture of any two or more thereof. In some embodiments, the hydrophilic solvent is a solid at room temperature. Such room temperature, solid hydrophilic solvents may alternatively be referred to as hydrophilic waxes. In some embodiments, the PEG has an average molecular weight of about 1,000 g/mol or greater. In some such embodiments, the PEG has an average molecular weight of from about 1,000 g/mol to about 20,000 g/mol. In other such embodiments, the PEG has an average molecular weight of from about 3,000 g$\mu$mol to about 20,000 g/mol. In some embodiments, the MPEG has an average molecular weight of about 1,000 g/mol or greater. In some such embodiments, the MPEG has an average molecular weight of from about 1,000 g/mol to about 20,000 g/mol. In other such embodiments, the MPEG has an average molecular weight of from about 3,000 g/mol to about 20,000 g/mol. In some embodiments, the PEO has an average molecular weight of about 20,000 g/mol or greater. In other embodiments, the PEO has an average molecular weight of from about 20,000 g/mol to about 300,000 g/mol.

Lipophilic solvents suitable for use in the embodied formulations may be liquid, semisolid, or solid at room temperature and may include, but are not limited to, a fatty acid such as, but no limited to, linoleic, linolenic, oleic, palmitostearic acids, and stearic acid; a medium chain glyceride such as, but not limited to, glyceryl mono-, di-, or tri-caprylic and capric acid esters, also known as medium chain mono-, di-, and triglycerides and sold under tradenames such as MIGLYOL® 812, LABRAFAC CC®, and CAPMUL® MCM; a long chain glyceride (of $C_{12}$-$C_{18}$ fatty acids) such as, but not limited to, corn oil, cottonseed oil, glyceryl behenate, glyceryl monooleate, glyceryl monostearate, glyceryl palmitostearate, olive oil, peanut oil, peppermint oil, safflower oil, sesame oil, and soybean oil; a ethyl ester of a fatty acid such as ethyl linoleate and ethyl oleate; DL-α-tocopherol; a propylene glycol fatty acid ester such as, but not limited to, propylene glycol mono- or di-laureate; a sorbitan fatty acid ester such as, but not limited to, sorbitan monolaurate, sorbitan monooleate, sorbitan monopalmitate, sorbitan monostearate, and sorbitan trioleate; a polyglyceryl fatty acid ester formed from various glyceryl ethers and fatty acids. Examples of polyglycerols used in esterification include diglycerol, tetraglycerol, hexaglycerol, decaglycerol, decaglycerol, and the like. Examples of fatty acids reacted with polyglycerols include oleic acid, linoleic acid, stearic acid, and the like. Examples of polyglyceryl fatty acid ester include PLUROL OLEIQUE CC 497 (polyglyceryl oleate; Gattefosse Co.), PLUROL STEARIQUE (polyglyceryl palmitostearate; Gattefosse Co.), DGMO-C (diglyceryl monooleate; Nikkol Co.), TETRAGLYN 1-0 (tetraglyceryl monooleate; Nikkol Co.), HEXAGLYN 1-0 (hexaglyceryl monooleate; Nikkol Co.), HEXAGLYN 5-0 (hexaglyceryl pentaoleate; Nikkol Co.), DECAGLYN 5-0 (Decaglyceryl pentaoleate; Nikkol Co.), DECAGLYN 10-0 (Decaglyceryl decaoleate; Nikkol Co.), and the like. In some embodiments, the lipophilic solvent is oleic acid.

Emulsifiers suitable for use in the embodied formulations may include, but are not limited to a sugar fatty acid ester; a polyoxyethylene sorbitan fatty acid ester such as, but not limited to, polysorbate 20, polysorbate 40, polysorbate 60, and polysorbate 80; a polyoxyethylene mono- and di-fatty acid ester including, but not limited to polyoxyl 40 stearate and polyoxyl 40 oleate; a mixture of polyoxyethylene mono- and di-esters of $C_9$-$C_{22}$ fatty acids and glyceryl mono-, di-, and tri-esters of $C_8$-$C_{22}$ fatty acids as sold under tradenames such as LABRASOL®, GELUCIRE® 44/14, GELUCIRE® 50/13, LABRAFIL® M 1944 CS, and LABRAFIL® M2125 CS; a polyoxyethylene castor oil compound such as, but not limited to, polyoxyl 35 castor oil, polyoxyl 40 hydrogenated castor oil, and polyoxyl 60 hydrogenated castor oil, as are sold under tradenames such as CREMOPHOR® ELP, CREMOPHOR® RH 40, and CREMOPHOR® RH 60, respectively; a polyoxyethylene alkyl ether including but not limited to polyoxyl 20 cetostearyl ether, and polyoxyl 10 oleyl ether; DL-α-tocopheryl polyethylene glycol succinate as may be sold under the tradename VITAMIN E TPGS®; a glyceryl mono-, di-, and tri-ester; a sucrose mono-, di-, and tri-ester; sodium dioctyl sulfosuccinate; sodium lauryl sulfate; or a mixture of any two or more thereof.

In some embodiments, the hydrophilic solvent is present at up to about 90 wt % based upon the total weight of the formulation. In other embodiments, the emulsifier is present at from about 5 wt % to about 50 wt % based upon the total weight of the formulation. In yet other embodiments, the lipophilic solvent is present at up to about 50 wt % based upon the total weight of the formulation. In some embodiments, the PEG is present at up to about 90 wt % based upon the total weight of the formulation.

In other embodiments, the solid formulations further comprise a polymeric carrier. Polymeric carriers of the invention are polymers suitable for use as a medium to deliver a drug substance. Thus, for example, a polymeric carrier may be an adsorbent carrier, disintegrant, binder, or diluent that will facilitate delivery of a drug substance to a subject. Polymeric carriers suitable for use in the embodied formulations include, but are not limited to, cellulose acetate phthalate, croscarmellose sodium, crospovidone, cyclodextrins, β-cyclodextrins, hydroxypropyl-β-cyclodextrins, γ-cyclodextrins, polyanionic-β-cyclodextrins, sulfobutylether-7-β-cyclodextrin, hydroxyethyl cellulose, hydroxypropyl cellulose, hydroxypropyl methylcellulose, hydroxypropyl methylcellulose phthalate, methylcellulose, microcrystalline cellulose, methacrylic acid copolymers, polymethacrylate polymers, poly(methacrylic acid-methyl methacrylate), poly(methacrylic acid-ethyl acrylate), ammonio methacrylate copolymer, poly(ethyl acrylate-methylmethacrylate-trimethylammonioethyl methacrylate chloride), poly(ethyl acrylate-methyl methacrylate), polyvinyl alcohol with an average molecular weight of from about 20,000 to about 200,000 g μmol, polyvinylpyrrolidine/vinylacetate, povidone with an average molecular weight of from about 2,500 to about 300,000 g/mol, sodium starch glycolate, starch, pregelatinized starch, or a mixture of any two or more thereof.

In other embodiments, the solid formulations further comprise a phospholipid carrier such as, but not limited to, diphosphatidylglycerol, a glycolipid, phosphatidic acid, phosphatidylcholine, phosphatidylethanol amine, phosphatidylglycerol, phosphatidylinositol, phosphatidylserine, sphingomyelin, or a mixture of any two or more thereof.

In some embodiments, the solid formulations further comprise an adsorbent carrier. Adsorbent carriers suitable for use in the embodied formulations include, but are not limited to aluminum magnesium silicate, aluminum silicate, bentonite, calcium carbonate, dicalcium phosphate, lactose, mannitol, microcrystalline cellulose, silicon dioxide, sodium starch glycolate, sorbitol, starch, sucrose, talc, or a mixture of any two or more thereof.

In addition to those ingredients and materials listed above, the solid formulations embodied herein may include additional ingredients. Such additional ingredients may be selected from, but are not limited to cross-linked povidone; cross-linked sodium carboxymethylcellulose; cross-linked β-cyclodextrin polymer; cross-linked dextran; croscarmellose; cross-linked carbomer; hydroxypropylmethylcellulose-acetate succinate; polyvinyl pyrrolidone; acrylic resins selected from homopolymers of acrylic acid, homopolymers of acrylic acid derivatives, copolymers of acrylic acid and acrylic acid derivatives; or a mixture of any two or more thereof. As used herein, acrylic acid derivatives are those compounds which contain an acrylate linkage that may be polymerized and can include, but is not limited to, methacrylic acid, methyl methacrylate, butyl methacrylate, dimethylaminoethyl methacrylate, trimethylammonioethyl methacrylate chloride, ethyl acrylate, and the like, or a mixture of any two or more thereof.

Solid formulations embodied herein may also include pharmaceutically acceptable additives such as an antioxidant, a coloring agent, a flavoring agent, a preservative, a sweetener, or a mixture of any two or more thereof. Antioxidants suitable for use in the embodied formulations include, but are not limited to, ascorbic acid, ascorbyl palmitate, butylated hydroxyanisole, butylated hydroxytoluene, ethylenediaminetetraacetic acid, salts of ethylenediaminetetraacetic acid, propyl gallate, sodium metabisulfite, vitamin E, esters of Vitamin E, or a mixture of any two or more thereof. Preservatives suitable for use in the embodied formulations include, but are not limited to, butylparaben, calcium sorbate, ethylparaben, methylparaben, monothioglycerol, potassium sorbate, propylparaben, sodium benzoate, sodium sorbate, sorbic acid, or a mixture of any two or more thereof. Sweeteners suitable for use in the embodied formulations include, but are not limited to, aspartame, glycyrrhizin salts, monoammonium glycyrrhizinate, saccharin, saccharin calcium, saccharin sodium, sugar, sucralose, or a mixture of any two or more thereof. Flavoring agents suitable for use in the embodied formulations include, but are not limited to, citric acid, menthol, peppermint oil, sodium citrate, vanillin, ethyl vanillin, or a mixture of any two or more thereof. Coloring agents suitable for use in the embodied formulations include, but are not limited to, FD&C blue #1, FD&C blue #2, FD&C green #3, FD&C red #3, FD&C red #4, FD&C yellow #5, FD&C yellow #6, D&C blue #4, D&C green #5, D&C green #6, D&C orange #4, D&C orange #5, iron oxides, or a mixture of any two or more thereof.

The amount of active pharmaceutical ingredient in solid formulations embodied herein varies with the intended application, and it is well within the skill of those in the art to determine the appropriate amount for any particular application based on the disclosure herein. In some embodiments of the solid formulations disclosed herein, the compound of Formula I, a pharmaceutically acceptable salt thereof, or a mixture of any two or more thereof, is present in an amount from about 0.1 wt % to about 40 wt % based upon the total weight of the formulation. In other such embodiments, the compound of Formula I, a pharmaceutically acceptable salt thereof, or a mixture of any two or more thereof, is present in an amount from about 0.2 wt % to about 20 wt % based upon the total weight of the formulation. In yet other embodiments, the compound of Formula I, a pharmaceutically acceptable salt thereof, or a mixture of any two or more thereof, is present in an amount from about 0.5 wt % to about 10 wt % based upon the total weight of the formulation.

In some embodiments, formulations of the present disclosure are solid solutions, or dispersions. In some such embodiments, formulations are contained within a capsule or a tablet. In some embodiments, the capsule is a hard shell capsule, a hard gelatin capsule, a soft gelatin capsule, natural pullulan capsule, or a hydroxypropyl methylcellulose shell capsule. In some embodiments, the total mass of the compound of Formula I, a pharmaceutically acceptable salt thereof, or a mixture of any two or more thereof, in the capsule or tablet ranges from about 1 mg to about 400 mg. In some embodiments, the capsule or tablet is coated with polymer or gelatin, or is encapsulated within a gelatin sheath. The capsule may be hard shell capsule and may further have a band-sealed head section and a body section. The capsules, or tablets may be encapsulated within a gelatin sheath and the gelatin sheath may further include a pharmaceutically acceptable coloring agent, a sweetener, an opacifier, or a mixture of any two or more thereof. Optionally, capsules or tablets may be coated with a sweetener, a cellulose polymer, a polymethacrylate polymer, polyvinyl acetate phthalate, a gelatin, or a mixture of any two or more. In embodiments where cellulose polymers are used to coat a capsule or tablet, the cellulose polymer may be selected from methylcellulose, hydroxyethylcellulose, hydroxyethylmethylcellulose, hydroxypropyl cellulose, hydroxypropylmethylcellulose, ethylcellulose, cellulose acetate phthalate, or a mixture of any two or more thereof. In embodiments where a polymethacrylate polymer is used to coat a capsule or tablet, the polymethacrylate polymer may be selected from methacrylic acid copolymers, poly(methacrylic acid-methylmethacrylate), poly(methacrylic acid-ethylacrylate), anmonio methacrylate copolymer, poly(ethyl acrylate-methylmethacrylate-trimethylammonioethyl methacrylate chloride), poly(ethyl acrylate-methyl methacrylate), or a mixture of any two or more thereof.

Methods

In another aspect, methods for producing formulations embodied herein are provided. Thus, in some embodiments, the methods comprise combining a compound of Formula I, a pharmaceutically acceptable salt thereof, or a mixture of any two or more thereof, with an ingredient selected from a hydrophilic solvent, a lipophilic solvent, an emulsifier, or a mixture of any two or more thereof to form a formulation. In other embodiments, the compound of Formula I, a pharmaceutically acceptable salt thereof, or a mixture of any two or more thereof, is further combined with an antioxidant, a coloring agent, a flavoring agent, a preservative, a sweetener, or a mixture of any two or more thereof. Suitable hydrophilic solvents, lipophilic solvents, emulsifiers, antioxidants, preservatives, sweeteners, flavoring agents, and coloring agents are as described above. In some embodiments, the hydrophilic solvent may be present at up to about 90 wt % based upon the total weight of the formulation. In some embodiments, the lipophilic solvent is present at up to about 50 wt % based upon the total weight of the formulation. In other embodiments, the emulsifier is present from about 10 wt % to about 50 wt % based upon the total weight of the formulation. In some embodiments, the antioxidant is present at up to about 1 wt % based upon the total weight of the formulation. In other embodiments, the sweetener is present at up to about 2 wt % based upon the total weight of the formulation. In other embodiments, the flavoring agent is present at up to about 2 wt % based upon the total weight of the formulation.

In some embodiments, the method of producing a formulation produces a liquid formulation. Such liquid formulations are described above. In some such embodiments of the methods, the hydrophilic solvent comprises a PEG, or a mixture of any two or more at up to about 90 wt % based upon the total weight of the formulation. In other such embodiments of the methods, the hydrophilic solvent comprises ethanol at up to about 15 wt % based upon the total weight of the formulation. In some embodiments, the methods further include forming at least one capsule with the formulation. In such capsules, the total mass of the compound of Formula I, a pharmaceutically acceptable salt thereof, or a mixture of two or more thereof ranges from about 1 mg to about 400 mg. In some such methods where a capsule is formed the capsule may be, but is not limited to, those capsules as described above. In some embodiments, the capsule may be band-sealed by band-sealing the capsule.

Sealing of capsules may be accomplished by many methods known to those of skill in the art. In some embodiments, sealing methods include spraying a mist of alcohol and water solution onto an inside lip of the head section to cause the hard shell capsule to form an adhesive gel, placing the head section in position over the body section to form the capsule, exposing the capsule to an elevated temperature of from about 35° C. to about 55° C., and allowing the adhesive gel to set. In other embodiments, the capsules are band-sealed.

In some embodiments, the methods embodied above produce a solid formulation. Such solid formulations are described above. In some embodiments of the method, the compound of Formula I, a pharmaceutically acceptable salt thereof, or a mixture of any two or more thereof, are combined in a formulation aid. In such embodiments, the formulation aid is selected from methanol, ethanol, or a mixture thereof. In some embodiments, the formulation aid is removed by spray-drying, and/or spray coating the formulation onto a pharmaceutically acceptable carrier to form a solid dispersion, and/or grinding the solid dispersion to form granules. In some embodiments, granules formed by such methods have a size of less than 250 μm. In some embodiments, the granules are screened (i.e., passed through a screen) to provide a uniform size distribution for the filling of a capsule with the granules. In embodiments where tablets are prepared instead of capsules, the granules are mixed with a carrier, an antioxidant, a coloring agent, an opacifier, and/or a mixture of any two or more thereof to form a second mixture, which is then pressed into the tablet.

In some embodiments, the methods comprise combining a compound of Formula I, a pharmaceutically acceptable salt thereof, or a mixture of any two or more thereof, with an ingredient selected from a hydrophilic solvent, a lipophilic solvent, an emulsifier, or a mixture of any two or more thereof to form a formulation, and melting the formulation to form a melted formulation. The melted formulation is then filled into a capsule, in one embodiment. Suitable capsules include both one- and two-piece capsules. In another embodiment, the melted formulation is spheronized to form a spheronized formulation that is then filled into a capsule, or pressed into a tablet form. As used herein, spheronized is used to refer to changing the shape of granules into spheres. Those of skill in the art will recognize many ways of producing spherically shaped granules, including mechanical methods. In yet another embodiment, the melted formulation is formed into a tablet. In yet another embodiment, the melted formulation is cooled to form a cooled formulation and the cooled formulation is processed by milling, sieving, mixing with an excipient, and/or by compressing into a tablet. In other embodiments, the melted formulation may be spray-dried or spray-congealed. Tablets formed by the disclosed methods are, in some embodiments, formed using a molding calendar with a pair of counter-rotating, chilled molding rolls. Thus, methods of preparing solid formuations include, but are not limited to hot melt methods as described above and below in the examples, and solvent dissolution/evaporation methods as described above and below in the examples.

Packaging

Pharmaceutical packagings are ubiquitous throughout the industry and most are well-suited to the formulations disclosed. Pharmaceutical packagings and/or containers for inventive formulations may include a storage vessel for one or more capsules, tablets, cachets, or lozenges of formulations embodied herein. Such embodiments of storage vessels include those made of any of a number of pharmaceutically compatible polymers, glasses, and metals, including for example, high density polyethylene. Disclosed pharmaceutical packagings include blister packaging, with at least one capsule, tablet, cachet, or lozenge of the formulation(s) disclosed herein. Further, such storage vessels may include a cotton or rayon coil and/or a heat induction seal. Suitable packaging is widely known to those of skill in the art and is not limiting of the broader aspects of this disclosure.

Methods of Treating

In another aspect, methods for treating cancer, inhibiting angiogenesis, and/or inhibiting RAF kinase in a subject are provided. In some embodiments, the method comprises administering to a subject in need of a cancer treatment, a formulation embodied herein. In some embodiments, the method comprises administering to a subject in need of an angiogenesis inhibitor, a formulation embodied herein. In other embodiments, methods comprise administering to a subject in need of an RAF kinase inhibitor, a formulation embodied herein. The formulations are typically administered in an amount sufficient to provide a $C_{max}$ of about 0.1 to about 10 μg/mL and/or an $AUC_{0\rightarrow\infty}$ of about 0.01 to about 10 mg*min/mL of the compound of Formula I, a pharmaceutically acceptable salt thereof, or a mixture of any two or more thereof, in the subject's plasma. Tables 2 and 6, below, show experimental data for several different formulations of API in fasted canines at the indicated dosage rates. However, while exemplified dosage rates were used in controlled studies, administered dosages of API in a subject may range from about 1.0 to about 50 mg per kilogram body mass of the subject.

Treatment regimens and methods of treating a subject with a compound of Formula I, a pharmaceutically acceptable salt thereof, or a mixture of any two or more thereof, are provided. In some embodiments, methods of treating cancer and/or inhibiting angiogenesis in a subject include administering a formulation of a compound of Formula I, a pharmaceutically acceptable salt thereof, or a mixture of any two or more thereof, once, twice, three times, four, or more times daily. In some embodiments, administration of such formulations includes treatment cycles of administering such formulations daily for 7, 14, 21, or 28 days, followed by 7 or 14 days without administration of the formulation. In other embodiments, the treatment cycle includes administration of the formulation daily for 7 days, followed by 7 days without administration of the compound. In some embodiments, the treatment cycle is repeated one or more times.

As noted above, a compound of Formula I, a pharmaceutically acceptable salt thereof, or a mixture of any two or more thereof, may be used for the treatment of various cancers in a subject. In some embodiments, the cancer to be treated is selected from, but is not limited to, bladder, breast, brain, carcinoma, chronic lymphoid leukemia, chronic myelogenous leukemia, colorectal, gastric, gastrointestinal stromal, glioma, lymphoma, melanoma, multiple myeloma, myeloproliferative disease, neuroendocrine, non-small cell lung, small cell lung, pancreatic, prostate, renal cell, small cell acute myelogenous leukemia, sarcoma, and/or thyroid cancers.

In any formulation, method, or packaging of the present invention it is contemplated where capsules are so provided, tablets may also be provided and where tablets are so provided, capsules may also be provided. Where tablets and/or capsules are so provided, cachets and/or lozenges may also be provided.

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present embodiments, thus generally described, will be understood more readily by reference to the following examples, which are provided by way of illustration and are not intended to be limiting of the present invention.

EXPERIMENTAL

Nomenclature for the compounds was provided using ACD Name version 5.07 software (Nov. 14, 2001) available from Advanced Chemistry Development, Inc., ChemInnovation NamExpert+NomenclatorTM brand software available from ChemInnovation Software, Inc., and AutoNom version 2.2 available in the ChemOffice® Ultra software package version 7.0 available from CambridgeSoft Corporation (Cambridge, Mass.). Some of the compounds and starting materials were named using standard IUPAC nomenclature.

Various starting materials may be obtained from commercial sources and prepared by methods known to one of skill in the art.

Example 1

Synthesis of {1-methyl-5-[2-(5-trifluoromethyl-1H-imidazol-2-yl)-pyridin-4-yloxy]-1H-benzoimidazol-2-yl}-(4-trifluoromethyl-phenyl)amine(Formula I)

Step 1

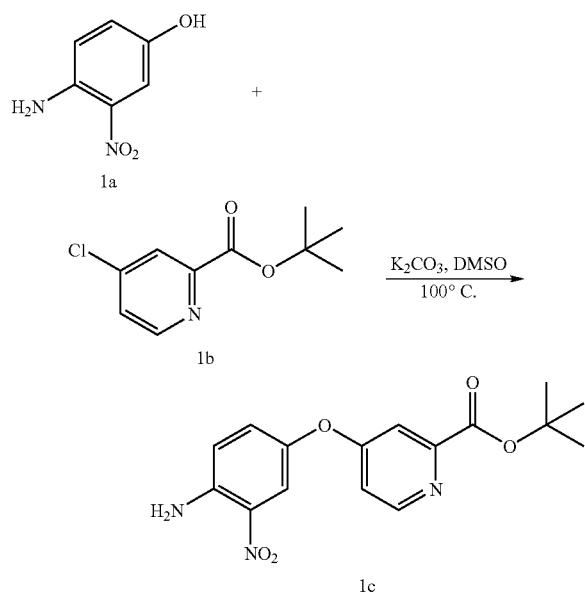

A 500 mL three-neck flask was fitted with a mechanical stirrer and charged with $K_2CO_3$ (4.15 g, 30 mmol). The vessel was sealed, evacuated, and flame dried. The apparatus was allowed to cool to rt and purged with argon. To the reaction flask was added 4-amino-3-nitrophenol 1a (3.08 g, 20 mmol), tert-butyl 4-chloropyridine-2-carboxylate 1b (5.2 g, 24 mmol) and dry DMSO (30 mL). The resulting mixture was stirred vigorously and heated to 100° C. for ~14 h. The reaction was poured over iced phosphate buffer (pH=7) and the reaction flask was rinsed well with MTBE and water. The combined biphasic mixture was filtered through Celite (>2 cm pad). The layers were partitioned and separated and the aqueous phase was extracted with MTBE (3×100 mL). The combined organic layers were washed with water (5×100 mL), dried ($MgSO_4$), and evaporated. The crude residue was adsorbed onto $SiO_2$, and purified by flash chromatography (4:1, 2:1, 1:1 hexanes/EtOAc) to furnish 4.92 g (14.9 mmol, 74% yield) of 1c as a yellow brown solid. $^1$H NMR (300 MHz, $CDCl_3$) δ 8.58 (d, J=5.8 Hz, 1 H), 7.90 (d, J=2.8 Hz, 1 H), 7.56 (d, J=2.5 Hz, 1 H), 7.17 (dd, J=2.8, 8.8 Hz, 1 H), 6.94 (dd, J=2.8, 5.8, Hz, 1 H), 6.91 (d, J=9.1 Hz, 1 H), 6.15 (br s, 2 H), 1.62 (s, 9 H); $^{13}$C NMR (75 MHz, $CDCl_3$) δ 165.8, 164.0, 151.8, 151.5, 143.4, 143.2, 131.5, 129.8, 121.0, 118.0, 114.2, 113.1, 83.0, 28.4; mp 163-166° C.

Step 2

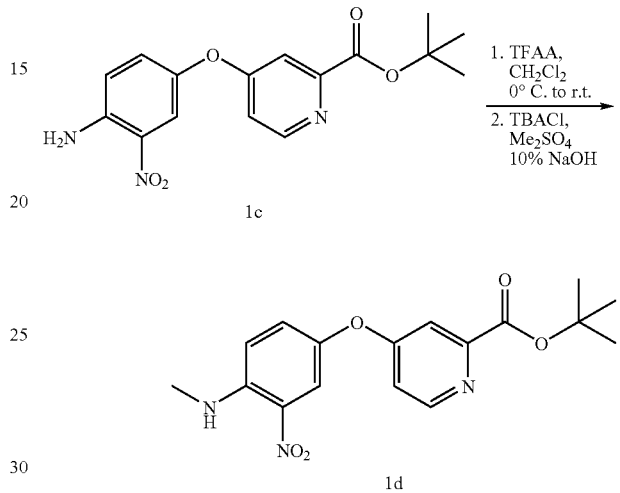

To a solution of 1c (5.62 g, 17 mmol) in $CH_2Cl_2$ (85 mL) at 0° C. was added TFAA (2.4 mL, 3.6 g, 17 mmol). The cooling bath was then removed and the reaction maintained at rt for 2 h. The reaction was cooled to 0° C. and TBACl (2.5 g, 8.5 mmol), $Me_2SO_4$ (3.2 mL, 4.3 g 34 mmol), and 10% NaOH (34 mL) were added. The resulting mixture was stirred vigorously for 4 h at rt. The reaction was diluted with water and the resulting layers were partitioned and separated. The aqueous phase was extracted with $CH_2Cl_2$ (3×100 mL), and the combined organic layers were washed with brine (2×100 mL), dried ($MgSO_4$), and evaporated. The crude residue was adsorbed onto silica gel and purified by flash chromatography (4:1, 2:1, 1:1, 1:2 hexanes/EtOAc) to give 4.5 g (13.0 mmol, 76%) of id as a yellow-orange solid. $^1$H NMR (300 MHz, $CDCl_3$) δ 8.54 (d, J=5.5 Hz, 1H), 8.04 (br d, J=4.7 Hz, 1 H), 7.93 (d, J=2.8 Hz, 1 H), 7.53 (d, J=2.5 Hz, 1 H), 7.25 (app dd, J=2.8, 9.1 Hz, 1 H), 6.91 (m, 2 H), 3.04 (d, J=4.9 Hz, 3 H), 1.59 (s, 9 H); $^{13}$C NMR (75 MHz, $CDCl_3$) δ 165.9, 164.1, 151.5, 144.7, 142.1, 130.4, 118.8, 115.5, 114.1, 112.9, 82.9, 30.4, 28.5; mp 187-189° C.

Step 3

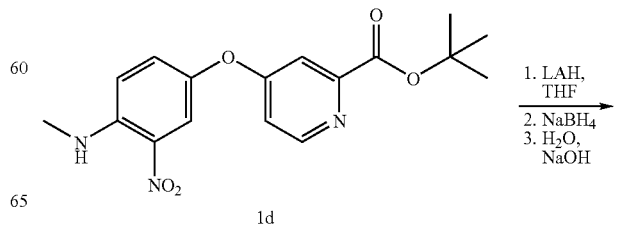

19
-continued

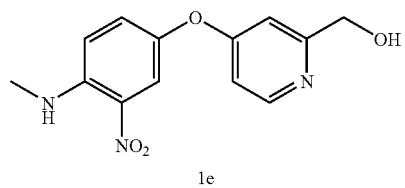

1e

A flame dried 500 mL three necked round bottom flask purged with N$_2$ was charged with LAH (3.0 g, 75 mmol) and dry THF (240 mL). The resulting suspension was cooled to 0° C. and 1d (20.7 g, 60 mmol) was slowly added while keeping the internal reaction temperature under 5° C. The reaction mixture was stirred at 0° C. for 2 h followed by stirring at rt overnight. NaBH$_4$ (2.27 g, 60 mmol) was added and the reaction mixture was stirred for an additional hour at rt. After the reaction was judged complete, the reaction mixture was treated with successive dropwise addition of water (3 mL), 15% NaOH (3 mL), and water (9 mL). The resulting mixture was filtered through Celite, and the remaining solids were washed with EtOAc and MeOH. The combined organic portions were evaporated and the resulting crude residue was adsorbed onto SiO$_2$ and purified by flash chromatography (97:3 CH$_2$Cl$_2$/MeOH) to afford 7.63 g (27.7 mmol, 46%) of a red-orange solid as 1e. $^1$H NMR (300 MHz, CDCl$_3$) δ 8.40 (d, J=5.5 Hz, 1 H), 8.05 (br s, 1 H), 7.96 (d, J=2.75 Hz, 1 H), 7.29 (d, J=2.75 Hz, 1 H), 6.92 (d, J=9.35 Hz, 1 H), 6.75 (m, 2 H), 4.68 (s, 2 H), 3.07 (d, J=5.23 Hz, 3 H).

Step 4

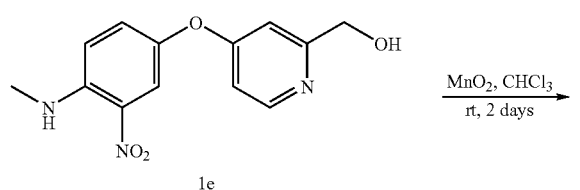

A 100 mL round bottom flask was charged with 1e (1.38 g, 5.0 mmol), MnO$_2$ (6.52 g, 75 mmol) and CHCl$_3$ (20 mL). The resulting suspension stirred at rt for 2 d. The reaction mixture was filtered through Celite, and the remaining solids were washed successively with CHCl$_3$ and EtOH. The combined organic portions were evaporated, absorbed onto silica gel, and purified by flash chromatography (98:2 CH$_2$Cl$_2$/MeOH) to give 790 mg (2.89 mmol, 58%) of an orange solid as 1f. $^1$H NMR (300 MHz, CDCl$_3$) δ 10.01 (s, 1 H), 8.64 (d, J=5.5 Hz, 1 H), 8.09 (br s, 1 H), 7.96 (d, J=2.75 Hz, 1 H), 7.37 (d, J=2.48 Hz, 1 H), 7.29 (d, J=2.75 Hz, 1 H), 7.08 (dd, J=2.47, 5.5 Hz, 1 H), 6.94 (d, J=9.35 Hz, 1 H), 3.08 (d, J=5.23 Hz, 3 H).

20
Step 5

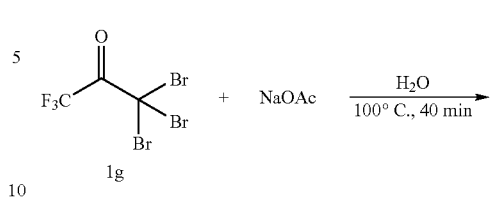

Ketone 1 g (Lancaster, 25.75 mL, 136.5 mmol) was added to a solution of sodium acetate (NaOAc) (22.4 g, 273 mmol) in H$_2$O (60 mL) and the resulting solution heated to 100° C. for 10 min. After cooling to rt, the solution of 1h was added to a suspension of 1f (25 g, 91 mmol) in NH$_4$OH (150 mL) and MeOH (450 ml) The resulting mixture was stirred at rt overnight. TLC (95:5 CH$_2$Cl$_2$/MeOH) showed complete consumption of 1f. The crude product was concentrated into an aqueous slurry, and partitioned with saturated Na$_2$CO$_3$ and CH$_2$Cl$_2$. The aqueous phase was extracted three times with CH$_2$Cl$_2$, and the combined organics washed with brine, dried with MgSO$_4$, and concentrated to give 31.6 g of 1i (83 mmol) as an orange solid (91% yield). No further purification was required.

Step 6

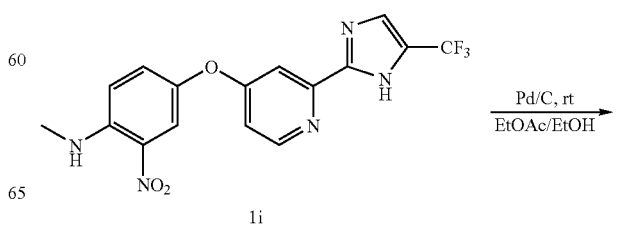

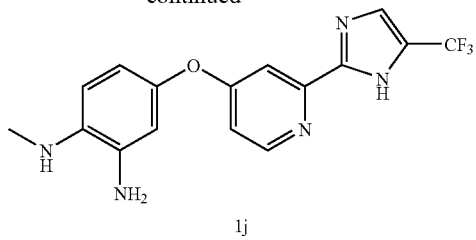

1j

A slurry of 1i (45.76 g, 120 mmol) in MeOH (220 mL) and EtOAc (200 mL) was sparged with $N_2$ for 20 min, and then charged with a suspension of 10% Pd/C (12.77 g, 120 mmol) in MeOH (60 mL). The reaction was purged with $H_2$ and maintained under a $H_2$ atmosphere for 2 d. The reaction was filtered through a pad of Celite and the collected solids were washed successively with MeOH and EtOAc. The combined organic filtrates were evaporated, and the resulting solid was azeotroped with $CH_2Cl_2$ and dried overnight, under vacuum, to give 40.17 g (115 mmol) of 1j as a tan powder (96% yield). LCMS m/z 336.1 ($MH^+$), $t_R$=1.8 min.

Step 7

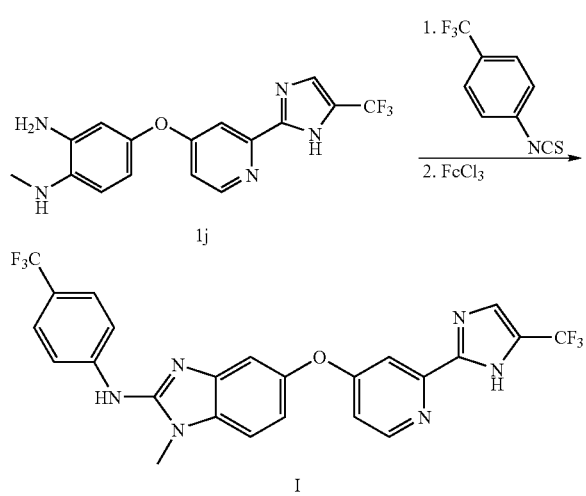

I 4-(Trifluoromethyl)phenyl isothiocyanate (23.37 g, 115 mmol) was added to a stirring solution of 1j (40.17 g, 115 mmol) in MeOH (460 mL) at rt. The reaction was maintained at rt for 16 h. After the reaction was judged complete, a solution of $FeCl_3$ (20.52 g, 126.5 mmol) in MeOH (50 mL) was added to the reaction and the resulting mixture was stirred at rt overnight. The crude reaction mixture was added to a 3 L separatory funnel containing EtOAc (750 mL) and water (750 mL). The layers were separated, and the aqueous phase was extracted with EtOAc (aqueous phase saved). The organic layers were combined, washed with saturated aqueous $Na_2CO_3$ solution, water, and brine, then dried ($MgSO_4$), and concentrated. The saved aqueous phase was made basic (pH=10) by addition of saturated aqueous $Na_2CO_3$ solution and the resulting slurry was added to a 3 L separatory funnel containing EtOAc (500 mL). The mixture was agitated and the resulting emulsion was filtered through filter paper, and the layers were then separated and the aqueous phase was extracted with EtOAc (2×500 mL). The organic layers were combined, washed with brine, then dried ($MgSO_4$), added to previously extracted material and concentrated. The combined product was triturated with $CH_2Cl_2$ (500 mL), adsorbed onto $SiO_2$ and purified by flash chromatography. A final trituration of material with $CH_2Cl_2$ produced the compound of Formula I as a pure, white solid. LCMS m/z 519.1 ($MH^+$); $^1H$ NMR (300 MHz, $CDCl_3$) δ 8.44 (d, J=5.5 Hz, 1 H), 7.75 (d, J=8.8 Hz, 2H), 7.61 (dd, J=2.2, 8.5 Hz, 1 H), 7.59 (d, J=8.8 Hz, 2 H), 7.56 (d, J=2.5 Hz, 1 H), 7.38 (app d, J=8.5 Hz, 1 H), 7.23 (d, J=1.9 Hz, 1 H), 6.96 (dd, J=2.2, 8.5 Hz, 1 H), 6.93 (dd, J=2.5, 5.5 Hz, 1 H), 3.76 (s, 3 H); LCMS m/z=519.0, $t_R$=2.57 min ($MH^+$); Anal. calc'd for $C_{24}H_{16}F_6N_6O$: C55.6, H3.11, N16.21; Found: C, 55.81; H, 3.43; N16.42; mp: 217-220° C. (dec.).

Example 2

Solubility of API

{1-Methyl-5-[2-(5-trifluoromethyl-1H-imidazol-2-yl)-pyridin-4-yloxy]-1H-benzoimidazol-2-yl}-(4-trifluoromethyl-phenyl)amine is practically insoluble in water. The aqueous solubility of the compound at various pHs is listed in the following Table 1.

TABLE 1

Solubility of API at different values of pH.

| pH | Solubility (mg/ml) |
|---|---|
| 1.36 | 0.7094 |
| 2.19 | 0.1253 |
| 3.75 | 0.0019 |
| 5.78 | 0.0004 |
| 10.13 | 0.0003 |
| 11.00 | 0.0003 |

Various non-aqueous solvents were evaluated to assess their suitability for use in formulating Formula I. Based on the results of the studies, the following suitable solvents were selected to formulate Formula I: PEG 400, oleic acid, polyoxyl 35 castor oil polysorbate 20 polysorbate 80, sorbitan monolaurate and sorbitan monooleate.

Example 3

Oral Solution Formulations of API

Canine models were used to study the in-vivo exposure of the API and various formulation approaches were explored in an attempt to increase the canine exposure. These formulation approaches included: micronization, solid dispersions, liquid and semisolid formulations that included co-solvent solutions, co-solvent solutions containing a polymer as a crystallization retardant, micelle forming formulations, SEDDS, and SMDDS.

Micronized powder formulations are prepared by initially dissolving the API (1.0 g) in acetone (20 mL) in a 200-mL round bottom flask. The flask is then held on a stirrer plate with a stirrer bar inside and the solution stirred at the highest speed setting. While continuously stirring, 5 mL of water is added to the flask every 10 sec up to a total of 100 mL of water. The resulting drug suspension is allowed to stir for an additional 20 minutes. The suspension is then vacuum filtered using a medium frit glass funnel filter. The solid material is dried overnight at 40° C., under vacuum (30 in. Hg). The solid material is then placed in a mortar and powdered with a pestle. Powder samples are then examined under polarized light microscope to verify crystallinity and particle size. When the average particle size is verified to be in the range of 3-5 microns, 50 mg of powder was filled into each of a number of HGCs.

Solid dispersion formulations are prepared by initially mixing and dissolving API and povidone (40 kD molecular weight), in 1:9 and 1:19 ratios, in methanol in 20-mL screw cap glass vials. Approximately 2 mL of MeOH is needed to completely dissolve 1.5 g of the 1:19 drug:povidone mixture. About 1 mL of MeOH is needed to completely dissolve 0.5 g of the 1:9 drug:povidone mixture. The resulting viscous solutions are placed on a stirrer plate. While stirring, the viscous solutions are partially evaporated with a stream of nitrogen gas. The extremely viscous solutions are then transferred to a vacuum oven at 40° C. The vacuum in the vacuum oven is increased until the first signs of bubbling appear. The vials are then allowed to stand in the vacuum oven overnight to allow for complete evaporation of the solvent. The resulting dry masses are crushed in the vials using a spatula. Half of a gram of the 1:9 mixtures and 1.0 g of the 1:19 mixture were filled into each of a number of HGCs.

Co-solvent formulations are prepared by dissolving 50 mg of API in 950 mg of a solvent or solvent mixture at 60° C., aided by sonication. One gram of each formulation is filled into an HGC. Additionally, hydrophilic polymers, HPMC and povidone are added to co-solvent solutions of API as potential crystallization inhibitors of the drug. HPMC (120 cps) is used at 2% w/w in 59% PEG 400 and 39% propylene glycol co-solvent formulations. HPMC is added gradually, but does not completely dissolve in these formulations resulting in suspensions that are filled into HGCs. Povidone of 10 kD and 40 kD molecular weights is dissolved in PEG 400 at 10, 20, 30, and 40% w/w and formulations are filled into HGCs. Povidone was also added to mixtures of either LABRASOL® and PEG 400 or Polysorbate (TWEEN®) and PEG 400.

Micellar formulations contain one or more surfactants dissolved in a solvent system that solubilizes API. All vehicles are prepared by weighing individual ingredients at the indicated percentages. API is added at 50 mg per 950 mg of the vehicle. Some of the surfactants in the study are solids at room temperature. Therefore, it is sometimes necessary to heat vehicle-drug mixtures while sonicating them to attain drug dissolution in the mixture. Heating the semisolid formulations (at temperatures up to 60° C.) is also sometimes necessary to fill the HGC with these formulations. One gram of each formulation is filled into each HGC.

SEDDS and SMEDDS formulations contain one or more surfactants, polar/hydrophilic component(s), and oil(s)/lipophilic component(s) (for example, fatty acids and/or fatty acid esters). In spite of the presence of an oil or oils, the formulations are isotropic, i.e., transparent one phase systems. Vehicles are prepared by weighing the individual excipients at the indicated percentages. API is added at 50 mg per 950 mg of the vehicle. Drug-vehicle mixtures are sonicated with heating (at temperatures up to 60° C.), to aid in drug dissolution. One gram of each formulation was filled into each HGC.

Table 2 shows $C_{max}$ (ng/mL) and $AUC_{0\to\infty}$ (ng·min/mL) data for various pharmaceutical formulations in fasted canines at a dosage level of 5 mg of API per kg of body mass.

TABLE 2

$C_{max}$ and $AUC_{0\to\infty}$ Values in Various Formulation Types

| Formulation Approach | $C_{max}$ ng/mL | $AUC_{0\to\infty}$ ng·min/mL |
|---|---|---|
| PEG 400 solution | 786 | 1509732 |
| Micronized powder | 10 | 47499 |
| Non-aqueous co-solvent solution 60% PEG 400/40% propylene glycol | 1005 | 1510273 |
| Non-aqueous co-solvent with polymer solution 59% PEG 400/39% Propylene glycol/2% HPMC | 375 | 767139 |
| Micellar solution 35% PEG 400/35% LABRASOL ®/30% CREMOPHOR ® EL | 996 | 1795874 |
| SEDDS Solution 33% polysorbate 80/33% oleic acid/34% PEG 400 | 2280 | 2431413 |
| SEDDS Solution 33% CREMOPHOR ® EL L/33% oleic acid/34% PEG 400 | 2880 | 2970518 |

CREMOPHOR ® EL: Polyoxyl 35 castor oil

Despite the smaller particle size of the micronized API powder (3-5 µm), the material yielded very poor in vivo pharmacokinetic parameters. These results are consistent with both the low solubility and slow dissolution rate of the API in an aqueous media. Aqueous solubility at pH 7 is below 1 µg/mL. Since the API is not bioavailable from a micronized solid dosage form, liquid formulations represent one alternative for improving bioavailability.

Exemplary liquid formulations for a water-insoluble compound include those formulations with a non-aqueous co-solvent system (for example, 60:40 PEG 400: propylene glycol) or a non-aqueous co-solvent system with a hydrophilic polymer (for example, 59:39:2 PEG 400: propylene glycol: HPMC). The latter formulation with HPMC yielded pharmacokinetic parameters that were poorer than those with the former formulation without the polymer. The addition of propylene glycol, as a co-solvent, to PEG 400 solutions, or micellar formulations both showed advantage over the 100% PEG 400 formulation in terms of bioavailability and dose-exposure proportionality.

An exploratory in vivo study employing the SEDDS and SMEDDS approaches indicated that the SEDDS and SMEDDS formulations could yield significantly higher API exposure in terms of $C_{max}$ and AUC in canine models. Due to the promising in vivo results obtained with the prototype SEDDS and SMEEDS formulations, further refinement work was done with this approach.

Table 3 lists materials used in the oral solution formulations disclosed in Table 4, along with vendors and abbreviations used. For each of formulations 1-33 in Table 4, the lipophilic component and emulsifier are weighed into a 40 mL glass vial and mixed thoroughly. The antioxidant, sweetener, and flavoring agent, if present in the formulation, are added and dissolved in the emulsifier-lipophilic component solution with the aid of sonication and vortexing. This placebo preparation is used to make the API solution formulations. A 50 mg/g (i.e., 5% w/w) mixture is prepared by dissolving 1.1 g of API in 20.9 g of each placebo preparation. This mixture is heated to about 45° C. in a water bath with intermittent sonication and vortexing until a clear solution is obtained. Similarly, a 5 mg/g (i.e., 0.5% w/w) solution is prepared by dissolving 0.1 g of API in 19.9 g of each placebo preparation. The solutions are filled into clear, 20 mL, glass vials and subjected to physical and chemical stability evaluation at 50° C./75% RH for two to three months. The stability of the formulations is summarized in Table 5.

TABLE 3

List of Materials Available from Various Vendors

| Material | Vendor | Abbreviation |
|---|---|---|
| Polyoxyl 40 hydrogenated castor oil (CREMOPHOR ® RH 40) | BASF | Crem. RH40 |
| Polyoxyl 35 castor oil (CREMOPHOR ® ELP) | BASF | Crem. EL |
| Polysorbate 80 (TWEEN ® 80) | Croda | Tween 80 |
| Polysorbate 20 (TWEEN ® 20) | Croda | Tween 20 |
| Oleic acid | Croda | Oleic acid |
| Mono-and di-glycerides of caprylic and capric acids (CAPMUL ® MCM) | ABITEC | MCM |
| PEG 400 | DOW | PEG 400 |
| Butylated hydroxytoluene | Eastman Chemicals | BHT |
| Butylated hydroxyanisole | Eastman Chemicals | BHA |
| Tocopherol | Spectrum | Tocopherol |
| Saccharin | Spectrum | Saccharin |
| Mono-ammonium salt of a triterpenoid saponin derived from a licorice root | MAFCO | MAGNASWEET ® |
| Peppermint oil | Arista Indus | Peppermint oil |
| Glass Vials | Eagle Picher | N/A |

TABLE 4

Microemulsion Formulations

| Form # | Emulsifier Type | % | Lipophilic Component Type | % | BHT % | BHA % | Tocopherol % | Saccharin % | Magnasweet % | Peppermint Oil % |
|---|---|---|---|---|---|---|---|---|---|---|
| 1 | Crem. RH40 | 20 | Oleic Acid | 20 | 0.02 | 0.02 | 0.05 | 0.4 | 0 | 0 |
| 2 | Crem. EL | 40 | MCM | 10 | 0.02 | 0 | 0 | 0 | 0 | 0 |
| 3 | Crem. EL | 40 | MCM | 20 | 0.02 | 0.02 | 0.05 | 0 | 0.1 | 0 |
| 4 | Crem. EL | 20 | MCM | 20 | 0 | 0 | 0.05 | 0 | 0.1 | 0.1 |
| 5 | Crem. EL | 40 | Oleic Acid | 20 | 0 | 0 | 0.05 | 0.4 | 0 | 0.1 |
| 6 | Crem. RH40 | 40 | Oleic Acid | 10 | 0 | 0.02 | 0 | 0.4 | 0.1 | 0.1 |
| 7 | Crem. RH40 | 20 | MCM | 10 | 0.02 | 0 | 0 | 0.4 | 0.1 | 0.1 |
| 8 | Tween 80 | 40 | MCM | 20 | 0 | 0 | 0 | 0.4 | 0 | 0 |
| 9 | Tween 80 | 20 | Oleic Acid | 10 | 0 | 0.02 | 0.05 | 0 | 0 | 0.1 |
| 10 | Tween 80 | 20 | MCM | 20 | 0.02 | 0.02 | 0 | 0.4 | 0 | 0.1 |
| 11 | Tween 80 | 20 | Oleic Acid | 10 | 0.02 | 0 | 0.05 | 0.4 | 0.1 | 0 |
| 12 | Tween 80 | 40 | Oleic Acid | 20 | 0.02 | 0.02 | 0 | 0 | 0.1 | 0.1 |
| 13 | Tween 80 | 40 | MCM | 10 | 0 | 0.02 | 0.05 | 0.4 | 0.1 | 0 |
| 14 | Tween 80 | 40 | Oleic Acid | 10 | 0.02 | 0 | 0.05 | 0 | 0 | 0.1 |
| 15 | Crem. EL | 40 | Oleic Acid | 20 | 0 | 0 | 0 | 0 | 0 | 0 |
| 16 | Crem. EL | 40 | Oleic Acid | 10 | 0.02 | 0 | 0.05 | 0.4 | 0 | 0 |
| 17 | Crem. EL | 20 | Oleic Acid | 10 | 0.02 | 0.02 | 0.05 | 0.4 | 0.1 | 0.1 |
| 18 | Crem. EL | 20 | Oleic Acid | 20 | 0 | 0 | 0 | 0 | 0 | 0 |
| 19 | Crem RH40 | 20 | Oleic Acid | 10 | 0 | 0.02 | 0 | 0 | 0 | 0 |
| 20 | Tween 20 | 30 | None | 0 | 0.02 | 0.02 | 0 | 0 | 0 | 0 |
| 21 | Crem. EL | 30 | Oleic Acid | 15 | 0.02 | 0 | 0 | 0.4 | 0.1 | 0.05 |
| 22 | Crem RH40 | 30 | Oleic Acid | 15 | 0.02 | 0 | 0 | 0.4 | 0.1 | 0.05 |
| 23 | Crem. EL | 30 | MCM | 15 | 0 | 0.02 | 0.05 | 0.4 | 0.1 | 0.05 |
| 24 | Tween 80 | 30 | Oleic Acid | 15 | 0 | 0.02 | 0 | 0.4 | 0.1 | 0.05 |
| 25 | Crem. EL | 40 | Oleic Acid | 20 | 0 | 0 | 0.05 | 0.4 | 0 | 0.1 |
| 26 | Tween 80 | 40 | Oleic Acid | 20 | 0.02 | 0.02 | 0 | 0 | 0.1 | 0.1 |
| 27 | Crem. EL | 40 | Oleic Acid | 20 | 0 | 0 | 0 | 0 | 0 | 0 |
| 28[1] | Tween 80 | 30 | None | 0 | 0.02 | 0.02 | 0 | 0 | 0 | 0 |
| 29 | Tween 80 | 40 | None | 0 | 0.02 | 0.02 | 0 | 0 | 0 | 0 |
| 30[2] | Tween 80 | 28 | Oleic acid | 14 | 0 | 0 | 0 | 0 | 0 | 0 |
| 31[2] | Crem. EL | 28 | Oleic acid | 14 | 0 | 0 | 0 | 0 | 0 | 0 |
| 32[3] | Crem. EL | 28 | Oleic acid | 14 | 0 | 0 | 0 | 0.4 | 0.1 | 0.05 |
| 33[3] | Crem. EL | 28 | Oleic acid | 14 | 0 | 0 | 0 | 0.4[4] | 0.1 | 0.05 |

Note:
All formulations were made up to 100% w/w with PEG 400.
All ingredients were based on % w/w.
[1] Contains 10% Ethanol.
[2] 3.74% API Concentration
[3] 4.67% API Concentration
[4] Contains Saccharin sodium

TABLE 5

Stability Information for Formulations Presented in Table 4

| Form # | 0.5% (5 mg/g) API Formulation | | | 5.0% (50 mg/g) API Formulation | | |
|---|---|---|---|---|---|---|
| | % API detected in Formulation | | Physical Appearance | % API detected in Formulation | | Physical Appearance |
| | Initial | 3 Month | 3 Month | Initial | 3 Month | 3 Month |
| 1 | 0.48 | — | Clear | 4.70 | — | Clear |
| 2 | 0.49 | 0.50 | Clear | 4.78 | 4.77 | Clear |
| 3 | 0.48 | 0.48 | Precipitation | 4.91 | 4.82 | Cloudy |
| 4 | 0.48 | 0.47 | Clear | 4.77 | 4.68 | Cloudy |
| 5 | 0.47 | 0.48 | Clear | 4.60 | 4.89 | Clear |
| 6 | 0.51 | — | Clear | 5.07 | — | Clear |
| 7 | 0.50 | 0.51 | Clear | 5.04 | 4.98 | Cloudy |
| 8 | 0.50 | — | Clear | 4.97 | — | Clear |
| 9 | 0.47 | 0.50 | Clear | 4.66 | 4.82 | Clear |
| 10 | 0.49 | 0.48 | Clear | 4.98 | 4.87 | Clear |
| 11 | 0.49 | — | Clear | 4.81 | — | Clear |
| 12 | 0.47 | 0.49 | Clear | 4.81 | 4.91 | Clear |
| 13 | 0.49 | — | Clear | 4.68 | — | Clear |
| 14 | 0.50 | — | Clear | 5.01 | — | Clear |
| 15 | 0.48 | 0.49 | Clear | 4.74 | 4.90 | Clear |
| 16 | 0.46 | 0.48 | Clear | 4.74 | 4.85 | Clear |
| 17 | 0.50 | 0.49 | Clear | 5.00 | 4.87 | Clear |
| 18 | 0.45 | 0.46 | Clear | 4.55 | 4.89 | Clear |
| 19 | 0.49 | — | Clear | 4.69 | — | Clear |
| 20 | 0.48 | 0.50 | Clear | 4.72 | 4.86 | Clear |
| 21 | 0.46 | 0.48 | Clear | 4.73 | 4.83 | Clear |
| 22 | 0.48 | 0.49 | Clear | 4.71 | 4.85 | Clear |
| 23 | 0.47 | 0.48 | Clear | 4.66 | 4.80 | Clear |
| 24 | 0.47 | 0.49 | Clear | 4.71 | 4.88 | Clear |
| 25 | 0.49 | 0.50 | Clear | 4.71 | 4.91 | Clear |
| 26 | 0.50 | — | Clear | 5.03 | — | Clear |
| 27 | 0.48 | 0.48 | Clear | 4.75 | 4.76 | Clear |
| 28[1] | 0.48 | 0.51 | Clear | 4.74 | 4.94 | Clear |
| 29 | 0.46 | 0.49 | Cloudy | 4.64 | 4.88 | Clear |
| 30[2] | — | — | — | 3.63 | 3.63 | Clear |
| 31[2] | — | — | — | 3.65 | 3.63 | Clear |
| 32[3] | — | — | — | 4.44 | 4.55 | Clear |
| 33[3] | — | — | — | 4.62 | — | — |

Note:
Not all samples were assayed at all time points, as indicated by "—"
Stability of Formulations 1-29 was evaluated at 50° C./75% RH
Stability of Formulations 30-33 was evaluated at 40° C./75% RH
[1]Contains 10% Ethanol.
[2]3.74% API Concentration
[3]4.67% API Concentration The solution formulation 30 was administered orally, once daily, in doses of 1, 3, 6, and 10 mg/kg/day of API for 28 days in male and female Beagle dogs. The plasma pharmacokinetic parameters are summarized in Table 6.

TABLE 6

Plasma Pharmacokinetic Parameters

| Day | Dose (mg/kg) | $t_{max}$ (h) | $C_{max}$ (µg/mL) | $AUC_{(0 \to 24)}$ (mg · min/mL) | $AUC_{(0 \to \infty)}$ (mg · min/mL) | $t_{1/2}^{a}$ (h) |
|---|---|---|---|---|---|---|
| 1 | 1 | 3.2 ± 0.6 | 0.26 ± 0.07 | 0.22 ± 0.06 | 0.61 ± 0.16 | 35 |
| | 3 | 3.0 ± 0.0 | 0.79 ± 0.17 | 0.64 ± 0.18 | 1.4 ± 0.6 | 22 |
| | 6 | 3.0 ± 0.0 | 1.4 ± 0.3 | 1.1 ± 0.3 | 1.9 ± 0.4 | 18 |
| | 10 | 3.0 ± 0.0 | 2.3 ± 0.7 | 1.9 ± 0.5 | 3.1 ± 0.8 | 16 |
| 14 | 1 | 2.8 ± 0.6 | 0.24 ± 0.05 | 0.15 ± 0.04 | N/A | 12 |
| | 3 | 2.5 ± 0.9 | 0.67 ± 0.09 | 0.32 ± 0.06 | N/A | 7.9 |
| | 6 | 2.3 ± 1.0 | 1.4 ± 0.3 | 0.64 ± 0.16 | N/A | 7.3 |
| | 10 | 2.8 ± 0.6 | 2.8 ± 0.7 | 1.5 ± 0.4 | N/A | 8.8 |
| 28 | 1 | 2.7 ± 0.8 | 0.27 ± 0.07 | 0.16 ± 0.05 | N/A | 12 |
| | 3 | 2.8 ± 0.6 | 0.69 ± 0.13 | 0.32 ± 0.07 | N/A | 8.2 |
| | 6 | 2.7 ± 0.8 | 1.5 ± 0.3 | 0.67 ± 0.17 | N/A | 7.7 |
| | 10 | 3.0 ± 0.0 | 3.0 ± 0.8 | 1.6 ± 0.4 | N/A | 9.1 |

Mean ± SD;
N/A = not applicable;
[a]Harmonic mean for $t_{1/2}$
Abbreviations:
$C_{max}$, maximum plasma concentration;
$t_{max}$, time to maximum concentration;
$AUC_{(0 \to 24)}$, area under the plasma concentration-time curve within a dosing interval of 24 h;
$AUC_{(0 \to \infty)}$, area under the plasma concentration-time curve between time 0 and time infinity;
$t_{1/2}$, plasma half-life.

Example 4

Hard Shell Capsule Formulations of API

The hard shell (gelatin and HPMC) capsules containing API, were manufactured by encapsulating the 0.7 mL API solution formulations in Formulations 1 and 2 (equivalent to 28 mg API) in size 00, clear, 2-piece hard-gelatin capsules (HGC) and size 00, clear, 2-piece HPMC capsules using a PROFILL® system (TORPAC®, Fairfield, N.J.), as outlined in Protocol 1, below. The solution-filled, hard shell capsules were sealed by: first spraying a mist of water/ethanol (1:1) solution onto the inside lip of the capsule head (moisturizing) to form an adhesive gel; placing the head in place over the capsule body tightly; exposing the formed capsule to 35-55° C. for 10-15 minutes (heating); and, finally, allowing the adhesive gel seal to set. In an actual manufacturing setting, the sealed capsules may further be band-sealed to prevent leakages, for tamper resistance, and/or for brand and dose identification; however, the capsules produced in these examples were not band-sealed. These prototype API, 28 mg, capsule formulations were manufactured for physical and chemical stability evaluation.

any changes in physical appearance and for recrystallization of API, from the fill formulation. Chemical stability was evaluated by assaying for the parent API, and its degradation products using suitable HPLC analytical procedures. Dissolution testing is carried out on capsules using a USP dissolution apparatus.

Several different types of two-piece hard capsules were used, and include, but are not limited to two-piece hard gelatin capsules (HOC), hydroxypropyl methylcellulose (HPMC) capsules, and natural pullulan Capsules (NPCAPS®). The capsules used may optionally contain opacifiers such as titanium dioxide and colorants. Commercial HGC filling machines are also used and include such machines as QUALICAPS F-40-LIQFIL SUPER40, QUALICAPS F-80-LIQFIL SUPER80, QUALICAPS F-120-LIQFIL SUPER120, QUALICAPS F-150-LIQFIL SUPER 150, and a CAPSUGEL CFS 1000 Capsule Filling and Sealing Machine. Commercial HGC sealing machines are used and include QUALICAPS S-40 HICAPSEAL and QUALICAPS S-100 HICAPSEAL machines.

The following formulations provided in Table 7 are for the purpose of further illustrating the compositions of API formulations that may be prepared for encapsulating into hard shell capsules in the laboratory, and are not to be taken in any way as limiting the scope of the present disclosure.

TABLE 7

Liquid Formulations

| Formulation | API | Polysorbate 20 | Oleic Acid | Cremophor® RH 40 | Labrasol® | Vitamin E TPGS | PEG 400 |
|---|---|---|---|---|---|---|---|
| 34 | 5 | 30 | 15 | — | — | — | 50 |
| 35 | 7.5 | 30 | 15 | — | — | — | 47.5 |
| 36 | 10 | 30 | 15 | — | — | — | 45 |
| 37 | 5 | 20 | 15 | 10 | — | — | 50 |
| 38 | 7.5 | 20 | 15 | 10 | — | — | 47.5 |
| 39 | 10 | 20 | 15 | 10 | — | — | 45 |
| 40 | 5 | 30 | 10 | — | — | — | 55 |
| 41 | 7.5 | 30 | 10 | — | — | — | 52.5 |
| 42 | 10 | 30 | 10 | — | — | — | 50 |
| 43 | 5 | — | — | — | 20 | — | 75 |
| 44 | 7.5 | — | — | — | 20 | — | 72.5 |
| 45 | 10 | — | — | — | 20 | — | 70 |
| 46 | 5 | — | — | — | 30 | — | 65 |
| 47 | 7.5 | — | — | — | 30 | — | 62.5 |
| 48 | 10 | — | — | — | 30 | — | 60 |
| 49 | 5 | — | 10 | — | 30 | — | 55 |
| 50 | 7.5 | — | 10 | — | 30 | — | 52.5 |
| 51 | 10 | — | 10 | — | 30 | — | 50 |
| 52 | 5 | — | — | — | — | 10 | 85 |
| 53 | 7.5 | — | — | — | — | 10 | 82.5 |
| 54 | 10 | — | — | — | — | 10 | 80 |
| 55 | 5 | — | — | — | — | 40 | 55 |
| 56 | 7.5 | — | — | — | — | 40 | 52.5 |
| 57 | 10 | — | — | — | — | 40 | 50 |

Note:
All amounts provided are in % w/w.

Protocol 1:
A. Dissolve API in the selected non-aqueous vehicle as shown in Formulations 1-33 in Table 4 and 34-57 in Table 7.
B. Mix to a clear solution.
C. Filter and deaerate.
D. Dispense into size 00 HGC or HPMC capsules.
E. Seal capsules with the aid of a hydroalcoholic solution
F. Seal capsules Physical and chemical stabilities of API, 28 mg formulations in hard shell capsules were evaluated under ambient conditions and at 40±2° C./75±5% RH (accelerated stability conditions). Physical stability of API capsules is evaluated for

Example 5

Soft Shell Capsule Formulations of API

Fill formulations containing API, were prepared by dissolving API in the solvent vehicles at concentrations ranging from 50 to 200 mg/g. Deionized water was introduced into each formulation at 4%, 8%, 10%, 12%, and 16% of formulation weight (e.g., 4 mg and 16 mg of water was added to 100 mg formulation for 4% and 16% water addition experiments, respectively) with gentle mixing. These levels of water were added to a formulation to mimic water migration from gelatin shell into encapsulated fill formulation and vice-versa during soft gelatin capsule manufacturing and subsequent equilibration processes, respectively. Physical stability of these formulations was evaluated at −20° C., 5° C., and ambient temperature. In this evaluation, the solutions were observed visually and microscopically at regular intervals for the presence of crystal formation of API. Chemical stability of these formulations was evaluated under ambient conditions and at 40±2° C./75±5% RH (accelerated stability conditions).

Solution fill formulations that showed stability under different storage conditions, as indicated by the absence of any API crystallization, were selected for further soft gelatin shell-fill compatibility studies. The physically stable API concentrations for each vehicle were based on formulations containing up to 8% water, as it was assumed to be the equilibrium water content in an encapsulated fill formulation.

API soft gelatin air-filled capsules are manufactured by encapsulating the 0.5 mL API solution formulations 31 and 35 into the air-fills. The air-fills are then sealed using molten gelatin. These prototype API air-filled capsule formulations are manufactured for physical and chemical stability evaluation.

Physical and chemical stability of API soft gelatin air-filled capsules is evaluated under ambient conditions and at 40±2° C./75±5% RH (accelerated stability conditions). Physical stability of API capsules is evaluated for any changes in physical appearance and for recrystallization of API from the fill formulation. Chemical stability is evaluated by assaying for the parent API and its degradation products using suitable HPLC analytical procedures. Dissolution testing is carried out on API capsules using a USP dissolution apparatus.

The soft gelatin capsules may be produced using a conventional rotary die process in which a molten mass of a gelatin sheath formulation is fed from a reservoir onto two chilled drums to form two sheaths of gelatin in a semi-molten state. These ribbons are then fed around rollers and brought together at a convergent angle in between a pair of roller dies that include opposed die cavities.

A fill formulation to be encapsulated is fed into a wedge-shaped component that in turn is injected into the die cavities covered by a gelatin ribbon. The gelatin ribbons are continuously conveyed between the dies, with a predetermined quantity of the fill formulation being entrapped between the sheets inside the die cavities. The sheets are then pressed together, and severed around each die so that opposed edges of the sheets flow together to form a continuous gelatin sheath around the entrapped fill formulation. These formed soft gelatin capsules are collected and further dried under controlled drying conditions. The dried soft gelatin capsules are then sorted, inspected, polished, printed, and packaged appropriately.

Various sheath formulations known those of skill in the art may be used to encapsulate the fill formulations of the present invention. Suitable sheath formulations may include gelatin, plasticizer(s), water, opacifier(s), colorants, taste modifiers, and moisture retaining agents. The gelatin will normally have a bloom strength (i.e., the force in grams required to press a 12.5 mm diameter plunger 4 mm into 112 g of a standard 6.667% w/v gelatin gel at 10° C.) in the range of from about 50 to about 300, and may be Type A or B gelatins or a mixture thereof. Limed bone, acid bone, bovine, porcine, fish gelatins, or a mixture of any two or more thereof, may be used. The plasticizer preferably is glycerin, sorbitol, sorbitol special (a mixture of sorbitol and sorbitan), maltitol, or a mixture of any two or more thereof.

Titanium dioxide is an opacifier typically used in gelatin sheath formulations. Taste modifiers include non-reducing sugars such as xylitol, maltitol, or Lycasin RTM. Some examples of suitable moisture retaining agents include celluloses, cellulose compounds, starches, starch compounds, vegetable gums, non-hygroscopic mono-, di- and oligosaccharides, and silicon dioxide. Various FD&C and D&C colorants may be used to impart the desired color to the capsule.

Example 6

Solid Dosage Formulations of API

The SEDDS and SMEDDS formulations, introduced above, yield a smaller size capsule that is easier to swallow when the desired API dose is smaller. However, the size of a capsule required to encapsulate larger volumes of SEDDS and SMEDDS formulations to deliver larger API doses may be too large to be swallowed, especially by younger and older patients. In order to be acceptable to the consumer, the pharmaceutical dosage form should be of a size that is easily swallowed. Compressed solid dosage forms (i.e., tablets and/or densified powders) would offer smaller size dosage forms even at larger doses. Thus, one objective of the present disclosure is to improve the rate of dissolution of the API in the gastrointestinal tract and thereby improve its bioavailability from these compressed solid dosage forms.

The primary solid dosage formulations are prepared using either hot melt methods or solvent dissolution/evaporation methods.

Hot Melt Methods. In hot melt methods, the primary formulation components are mixed in a blender to form a powder blend, melted and the molten mass is mixed thoroughly to obtain a homogeneous drug solution or drug dispersion. Alternatively, mixing and melting operations on the powder blend may also be carried out in a hot melt extruder, preferably in a single or twin-screw extruder at a temperature range from about 40 to about 160° C. The molten mass is then filled directly into two-piece capsules, or spheronized first and then filled into two-piece hard capsules. The molten mass could also be molded in the desired shape tablet using a molding calendar consisting of a pair of counter-rotating chilled molding rolls. Alternatively, the molten mass is cooled and processed further through milling, sieving, mixing with other excipients, and compressing into a tablet dosage formulation.

Formulation 58

Povidone and API are dissolved in a molten carrier of PEG 8000 and polyoxyl 150 stearate at 70±10° C. with thorough mixing using a high shear mixer. The resulting solution is transferred into the bowl of a VMA10 high shear granulator (available from L.B. Bohle, Inc.), maintained at 70±10° C. Alternatively, the solution could be prepared directly in the bowl of the VMA10 at 70±10° C. While mixing the solution with the agitator, crospovidone is added slowly to the bowl. Once the addition of crospovidone is complete, the contents of the bowl are mixed thoroughly to obtain a homogeneous dispersion. The dispersion is then cooled down slowly to room temperature while mixing with the agitator continuously, and with the chopper intermittently. The formed granules of the primary formulation are then sized and screened. The screened granules (334 mg; equivalent to 50 mg API) are then filled into Size 0 two-piece hard gelatin capsules using a PROFILL® system (available from TORPAC®, Fairfield, N.J.). Alternatively, the screened granules are mixed with crospovidone, microcrystalline cellulose, and silicon dioxide in a V-blender. The material is compressed into tablets of 400 mg average weight (equivalent to 50 mg API). The tablets and capsules are finally packaged into HDPE bottles or blister packs.

| Primary Formulation | |
|---|---|
| Ingredient | % w/w |
| API | 15 |
| PEG 8000 | 50 |
| Povidone K-17 | 5 |
| Crospovidone | 20 |
| Polyoxyl 150 stearate | 10 |
| TOTAL | 100 |

| Tablet Formulation | |
|---|---|
| Ingredient | Amount per Tablet |
| Primary Formulation | 334 mg (Equivalent to 50 mg API) |
| Crospovidone | 46 mg |
| Microcrystalline cellulose | 15 mg |
| Silicon dioxide | 5 mg |
| TOTAL | 400 mg |

Formulation 59

This formulation was prepared in a manner analogous to that used for Formulation 58.

| Primary Formulation | |
|---|---|
| Ingredient | % w/w |
| API | 12.5 |
| PEG 20000 | 50.0 |
| Sodium Starch Glycolate | 20.0 |
| Vitamin E TPGS | 10.0 |
| Oleic Acid | 7.5 |
| TOTAL | 100 |

| Tablet Formulation | |
|---|---|
| Ingredient | Amount per Tablet |
| Primary Formulation | 400 mg (Equivalent to 50 mg API) |
| Sodium Starch Glycolate | 90 mg |
| Silicon Dioxide | 10 mg |
| TOTAL | 500 mg |

Formulation 60

API was dissolved in a molten carrier of MPEG 5000 (MPEG 5000; Dow Chemical Co.) and DL-α-tocopheryl polyethylene glycol 1000 succinate (Vitamin E TPGS™; Eastman Chemical Co.) at 60±10° C. with thorough mixing using a high shear mixer. The resulting solution was transferred into the bowl of a VMA10 high shear granulator (L.B. Bohle Inc.), maintained at 60±10° C. Alternatively, the solution could be prepared directly in the bowl of the VMA10 at 60±10° C. While mixing the solution with the agitator, crospovidone is slowly added to the bowl. Once the addition of crospovidone is complete, the contents of the bowl are mixed thoroughly to obtain a homogeneous dispersion. The dispersion is then cooled down slowly to room temperature while mixing with the agitator continuously, and with the chopper intermittently. The formed granules of the primary formulation, now a solid dispersion, are then sized and screened. The screened granules are mixed with crospovidone and talc in a V-blender. The material is compressed into tablets of 600 mg average fill weight (equivalent to 50 mg API). The tablets are then packaged into HDPE bottles or blister packs.

| Primary Formulation | |
|---|---|
| Ingredient | % w/w |
| API | 12.5 |
| MPEG 5000 | 35 |
| Crospovidone | 37.5 |
| Vitamin E TPGS | 15 |
| TOTAL | 100 |

| Tablet Formulation | |
|---|---|
| Ingredient | Amount per Tablet |
| Primary Formulation | 400 mg (Equivalent to 50 mg API) |
| Crospovidone | 180 mg |
| Talc | 20 mg |
| TOTAL | 600 mg |

Formulation 61

API is dissolved in a molten carrier of PEG 1000 and GELUCIRE® 44/14 at 70±10° C. with thorough mixing using a propeller blade. The resulting solution is cooled to 50±10° C., and a 250 mg aliquot of the hot molten solution is then manually filled into a size 2 hard gelatin capsule (HGC) using a positive displacement pipette. The filled, hard shell capsules are sealed by: first spraying a mist of water/ethanol (1:1) solution onto the inside lip of the capsule head (moisturizing) to form an adhesive gel; placing the head in place over the capsule body tightly; exposing the formed capsule to 35-55° C. for 10-15 minutes (heating); and finally allowing the adhesive gel seal to set. Each capsule thus contains 50 mg of API and 200 mg of carrier. The capsules are packaged into HDPE bottles.

| Primary Formulation | |
|---|---|
| Ingredient | % w/w |
| API | 20 |
| PEG 1000 | 40 |
| GELUCIRE ® 44/14 | 40 |
| TOTAL | 100 |

| Tablet Formulation | |
|---|---|
| Ingredient | Amount per Tablet |
| Primary Formulation Capsule Fill | 250 mg (Equivalent to 50 mg API) 250 mg |

Solid Solutions and Dispersion Using Solvent Dissolution/Evaporation Methods. In solvent dissolution/evaporation methods, the primary formulation components are mixed and dissolved into a common solvent. The solvent is removed from the mixture using either conventional tray drying under vacuum or spray drying. The solid mass so obtained is ground, sieved, and filled into two-piece hard capsules. Alternatively, these formulations may be further processed through milling, sieving, and/or mixing with other excipients, and compressing into a tablet dosage formulation.

Formulation 62

Povidone and API are dissolved in a formulation aid such as MeOH (2 mL of MeOH for every 100 mg API) at 70±10° C. in a round-bottom flask with mixing until a clear solution was obtained. PEG 8000 is then added and the mixture vigorously mixed. The flask containing the solution is then attached to a rotary evaporator and the MeOH removed under vacuum at 70±10° C. After the removal of MeOH from the mixture, the flask is then placed in a cold-water bath and the vacuum maintained for another 2 hours. The resulting solid is transferred from the flask onto a tray and dried under vacuum at room temperature for another 6 hours to remove any residual MeOH. The dispersion is then ground and granules of less than 250 microns in size are collected by screening for further studies.

The screened granules (400 mg; equivalent to 100 mg API) are filled into a size 0 two-piece hard gelatin capsule. Alternatively, the screened granules are mixed with crospovidone, microcrystalline cellulose (MCC), and silicon dioxide in a mini blender. The material is then compressed into tablets of 550 mg average weight (equivalent to 100 mg API). The tablets and capsules are packaged into HDPE bottles, or blister packs.

| Primary Formulation | |
|---|---|
| Ingredient | % w/w |
| API | 25 |
| PEG 8000 | 50 |
| Povidone K-30 | 25 |
| Methanol | Formulation aid[1] |
| TOTAL | 100 |

[1]Formulation aids are completely removed after processing.

| Tablet Formulation | |
|---|---|
| Ingredient | Amount per Tablet |
| Primary Formulation | 400 mg (Equivalent to 100 mg API) |
| Crospovidone | 100 mg |
| Microcrystalline Cellulose | 40 mg |
| Silicon dioxide | 10 mg |
| Total | 550 mg |

Any of a number of appropriate apparatuses are available to assist in blending, extrusion, sizing, encapsulation, sealing, filling, pressing, and other processes in preparing pharmaceutical formulations. Various types of two-piece hard capsules include, but are not limited to, two-piece HGCS, HPMC capsules, and natural pullulan capsules. All such capsule shells may contain opacifiers such as talc and titanium dioxide, and colorants. Listed herein are numerous apparatuses that were used in the experimental processes, but are not intended to be limiting in any manner as many different makes, models, and manufacturers exist in the industrial setting. For example, blending equipment may include PK V-Blenders, cone tumble blenders, fluid bed granulators available from Glatt Air Techniques and Niro Pharma System, planetary mixers, and ribbon blenders. Hot melt extrusion equipment may include ZSE 18 HP; ZSE 27 HP; ZSE 40 HP; Micro 18; and Micro 27 co-rotating and counter-rotating twin screw extruders available from American Leistritz Extruder Corporation); single screw 19/20 DN, and twin screw DSE 25 & DSE 35 co-rotating & counter rotating twin screw extruders from Brabender Measurement & Control Systems); and Caleva Extruders Models 20, 40, and 100 available from Caleva Process Solutions Ltd. Sizing equipment may include Comil Sizers available from Quadro; Hammermill sizers available from Fitzpatrick; Oscillator sizers from a number of vendors. Hard capsule filling machines for filling a molten mass such as the QUALICAPS F-40-LIQFILsuper40, QUALICAPS F-80-LIQFILsuper80, QUALICAPS F-120-LIQFILsuper120, QUALICAPS F-150-LIQFILsuper150, and the Capsugel CFS 1000 Capsule Filling and Sealing Machine. Hard capsule sealing machines such as the QUALICAPS S-40 HICAPSEAL and the QUALICAPS S-100 HICAPSEAL. Hard capsule filling machines for filling solid powders include the MG from MG2, the GKF from Bosch, and the Zanasi from IMA. Tablet press equipment available from Manesty, Fette, and Courtoy. Tablet coating equipment available from Niro Pharma Systems such as SIROCCO®; MULTI-PROCESSOR®; MP-MICRO®; STREA-1®; and MP-1 MULTI-PROCESSOR® and Glatt such as their fluid bed granular/dryer/coater.

Further Modifications of the Tablet Dosage Formulations. Tablet dosage forms may also be coated to improve appearance, elegance, and/or taste. In some cases, the tablet is coated with a sugar, cellulose polymer, and/or polymethacrylate polymer. Some examples of coating materials available commercially are under the trade names OPADRY®, SURELEASE®, AQUACOAT®, and EUDRAGIT®. The coating material may further contain a pharmaceutically acceptable coloring agent and/or a pharmaceutically acceptable opacifier, including but not limited to opacifiers such as titanium dioxide or talc. Alternatively, the tablet formulation may be coated with gelatin or encapsulated within a gelatin sheath. The gelatin sheath material may further contain a pharmaceutically acceptable coloring agent and/or a pharmaceutically acceptable opacifier.

What is claimed is:
1. A formulation, comprising:
 a pharmaceutically acceptable salt of a compound of Formula I or a tautomer thereof, or a mixture of any two or more of the compound and salts; a hydrophilic solvent comprising ethanol, a polyethylene glycol, or a mixture thereof,
 a lipophilic solvent comprising a fatty acid, and
 an emulsifier;
 wherein the compound of Formula I is:

and wherein the pharmaceutically acceptable salt, or the mixture of any two or more of the compound and salts thereof, is in an amount of from 0.1 wt % to 40 wt % based upon the total weight of the formulation.

2. The formulation of claim 1, wherein the hydrophilic solvent is polyethylene glycol.

3. The formulation of claim 1, wherein the emulsifier is selected from the group consisting of a sugar fatty acid ester; a sucrose mono-, di-, or tri-fatty acid ester; a polyoxyethylene castor oil compound; a polyoxyethylene sorbitan fatty acid ester; a polyoxyethylene mono- or di-fatty acid ester; a polyoxyethylene alkyl ether; a glyceryl mono-, di-, or tri-fatty acid ester; a mixtures of polyoxyethylene mono- or di-ester of a $C_8$-$C_{22}$ fatty acid; and a glyceryl mono-, di-, or tri-ester of a $C_8$-$C_{22}$ fatty acid, or a mixture of any two or more thereof.

4. The formulation of claim 1, wherein the lipophilic solvent is oleic acid.

5. The formulation of claim 1, wherein the emulsifier is selected from the group consisting of polyoxyl 35 castor oil, polyoxyl 40 hydrogenated castor oil, polyoxyl 60 hydrogenated castor oil, polysorbate 20, polysorbate 40, polysorbate 60, polysorbate 80, polyoxyl 40 stearate, polyoxyl 40 oleate, polyoxyl 20 cetostearyl ether, polyoxyl 10 oleyl ether, and DL-α-tocopheryl polyethylene glycol succinate, or a mixture of any two or more thereof.

6. The formulation of claim 1, further comprising an antioxidant, a coloring agent, a cyclodextrin, a flavoring agent, a preservative, a sweetener, or a mixture of any two or more thereof.

7. The formulation of claim 2, wherein the polyethylene glycol has an average molecular weight of from 100 g/mol to 1,000 g/mol.

8. The formulation of claim 1, wherein the amount of the pharmaceutically acceptable salt, or the mixture of any two or more of the compound and salts thereof, is from 0.2 wt % to 20 wt % based upon the total weight of the formulation.

9. The formulation of claim 8, wherein the amount of the pharmaceutically acceptable salt, or the mixture of any two or more of the compound and salts thereof, is from 0.5 wt % to 10 wt % based upon the total weight of the formulation.

10. The formulation of claim 1, wherein the hydrophilic solvent is present at up to 90 wt % based upon the total weight of the formulation.

11. The formulation of claim 1, wherein the emulsifier is present at from 5 wt % to 50 wt % based upon the total weight of the formulation.

12. The formulation of claim 1, wherein the lipophilic solvent is present at up to 50 wt % based upon the total weight of the formulation.

13. The formulation of claim 1, wherein the formulation is contained within a capsule.

14. The formulation of claim 13, wherein the total mass of the pharmaceutically acceptable salt, or the mixture of any two or more of the compound and salts thereof, in the capsule ranges from 1 mg to 400 mg.

15. The formulation of claim 1, wherein the hydrophilic solvent comprises ethanol.

16. The formulation of claim 15, wherein the ethanol is present at up to 15 wt % based upon the total weight of the formulation.

17. The formulation of claim 1, wherein the polyethylene glycol is present at up to 90 wt % based upon the total weight of the formulation.

18. A method of preparing a formulation comprising:
(a) combining a pharmaceutically acceptable salt of a compound of Formula I or a tautomer thereof, or a mixture of any two or more of the compound and salts thereof, with a hydrophilic solvent comprising ethanol, a polyethylene glycol or a mixture thereof, a lipophilic solvent comprising a fatty acid, and an emulsifier, to form the liquid formulation;
wherein the compound of Formula I is:

and wherein the pharmaceutically acceptable salt, or the mixture of any two or more of the compound and salts thereof, is in an amount of from 0.1 wt % to 40 wt % based upon the total weight of the formulation.

19. The method of claim 18, wherein the hydrophilic solvent is present at up to 90 wt % based upon the total weight of the formulation.

20. The method of claim 18, wherein the emulsifier is present at from 10 wt % to 50 wt % based upon the total weight of the formulation.

21. The method of claim 18, wherein the lipophilic solvent is present at up to 50 wt % based upon the total weight of the formulation.

22. The method of claim 18, further comprising combining the pharmaceutically acceptable salt or the mixture of any two or more of the compound and salts thereof, the hydrophilic solvent, the lipophilic solvent, and the emulsifier, with an antioxidant, a coloring agent, a flavoring agent, a preservative, a sweetener, or a mixture of any two or more thereof.

23. The method of claim 22, wherein the hydrophilic solvent comprises a polyethylene glycol, or a mixture of any two or more thereof at up to 90 wt % based upon the total weight of the formulation.

24. The method of claim 22, wherein the hydrophilic solvent comprises ethanol at up to 15 wt % based upon the total weight of the formulation.

25. The method of claim 22, further comprising (b) forming at least one capsule with the formulation.

26. The method of claim 25, wherein the total mass of the pharmaceutically acceptable salt, or the mixture of any two or more thereof, in the capsule is from 1 mg to 400 mg.

27. The method of claim 25, wherein the capsule is a gelatin capsule or a hard shell capsule.

28. A formulation, comprising:
a pharmaceutically acceptable salt of a compound of Formula I:

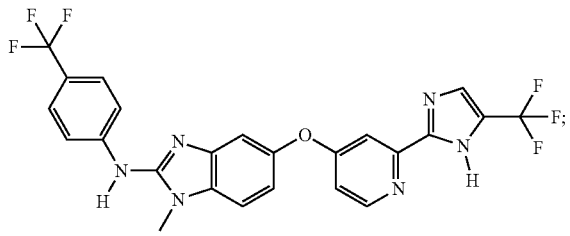

or a pharmaceutically acceptable salt of a tautomer of the compound of Formula I, or a mixture of any two or more of the compound and salts thereof in an amount of from 0.1 wt % to 40 wt % based upon the total weight of the formulation; and polyethylene glycol 400, oleic acid, and an emulsifier;

wherein the emulsifier is selected from the group consisting of mono- and di-glycerides of caprylic and capric acids, polyoxyl 40 hydrogenated castor oil, polyoxyl 35 castor oil, polysorbate 80, and polysorbate 20, or a mixture thereof.

29. The formulation of claim 28, wherein the emulsifier is polysorbate 80.

30. The formulation of claim 28, wherein the emulsifier is polyoxyl 35 castor oil.

31. The formulation of claim 28, further comprising a sweetener and a flavoring agent.

32. The formulation of claim 31, wherein the sweetener comprises saccharin and monoammonium glycyrrhizinate, and the flavoring agent comprises peppermint oil.

33. The formulation of claim 28, wherein polyethylene glycol 400 is present at up to 90 wt % based upon the total weight of the formulation.

34. The formulation of claim 28, wherein oleic acid is present at up to 50 wt % based upon the total weight of the formulation.

35. The formulation of claim 28, wherein the emulsifier is present at from 10 wt % to 50 wt % based upon the total weight of the formulation.

36. The formulation of claim 28, wherein the amount of the pharmaceutically acceptable salt, or the mixture of any two or more of the compound and salts thereof, is from 0.5 wt % to 10 wt % based upon the total weight of the formulation.

37. A method of preparing the formulation of claim 28 comprising combining the pharmaceutically acceptable salt, or the mixture of any two or more of the compound and salts thereof, with polyethylene glycol 400, oleic acid, and the emulsifier to form the liquid formulation.

38. A liquid formulation, comprising:
a pharmaceutically acceptable salt of the compound of Formula I or a pharmaceutically acceptable salt of a tautomer of the compound of Formula I in an amount of from 0.1 wt % to 40 wt % based upon the total weight of the formulation,
a hydrophilic solvent comprising ethanol, a polyethylene glycol, or a mixture thereof,
a lipophilic solvent comprising a fatty acid, and
an emulsifier;
wherein the compound of Formula I is:

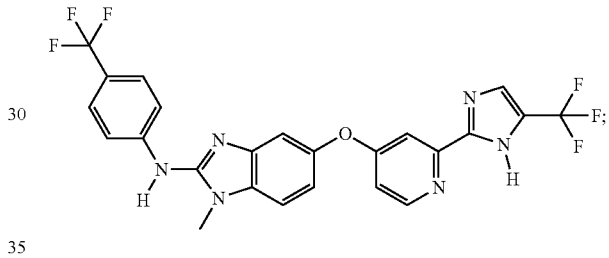

39. The formulation of claim 1, wherein the formulation is a liquid formulation.

* * * * *

UNITED STATES PATENT AND TRADEMARK OFFICE
CERTIFICATE OF CORRECTION

| | | |
|---|---|---|
| PATENT NO. | : 8,455,662 B2 | Page 1 of 1 |
| APPLICATION NO. | : 12/374383 | |
| DATED | : June 4, 2013 | |
| INVENTOR(S) | : Hashash et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 844 days.

Signed and Sealed this
Thirtieth Day of December, 2014

Michelle K. Lee
*Deputy Director of the United States Patent and Trademark Office*